US012614552B1

(12) United States Patent
Srinivasan et al.

(10) Patent No.: US 12,614,552 B1
(45) Date of Patent: Apr. 28, 2026

(54) JOINT ASR AND SPEAKER ERROR CORRECTION POST-PROCESSING

(71) Applicant: Amazon Technologies, Inc., Seattle, WA (US)

(72) Inventors: Sundararajan Srinivasan, Mountain View, CA (US); Rohit Paturi, Newark, CA (US); Katrin Kirchhoff, Seattle, WA (US); Marc Helbing, Aachen (DE); Sumit Kumar, Issaquah, WA (US); Xiang Li, Cambridge (GB)

(73) Assignee: Amazon Technologies, Inc., Seattle, WA (US)

( * ) Notice: Subject to any disclaimer, the term of this patent is extended or adjusted under 35 U.S.C. 154(b) by 352 days.

(21) Appl. No.: 18/331,527

(22) Filed: Jun. 8, 2023

(51) Int. Cl.

| | |
|---|---|
| ***G10L 17/14*** | (2013.01) |
| ***G10L 17/02*** | (2013.01) |
| ***G10L 17/22*** | (2013.01) |
| ***G16H 10/60*** | (2018.01) |

(52) U.S. Cl.
CPC .............. *G10L 17/14* (2013.01); *G10L 17/02* (2013.01); *G10L 17/22* (2013.01); *G16H 10/60* (2018.01)

(58) Field of Classification Search
CPC ......... G10L 17/14; G10L 17/02; G10L 17/22; G16H 10/60
See application file for complete search history.

(56) References Cited

U.S. PATENT DOCUMENTS

| | | | |
|---|---|---|---|
| 6,029,124 | A | 2/2000 | Gillick et al. |
| 12,062,016 | B2 | 8/2024 | Almendro et al. |
| 2003/0144837 | A1 | 7/2003 | Basson et al. |
| 2014/0025380 | A1 * | 1/2014 | Koch ...................... G10L 15/30 704/E15.005 |
| 2014/0236626 | A1 * | 8/2014 | Reddy Bynagari .... G16H 10/60 705/3 |
| 2016/0275952 | A1 | 9/2016 | Kashtan et al. |
| 2018/0074785 | A1 * | 3/2018 | Ohmura ................ G06F 3/0487 |
| 2018/0082692 | A1 | 3/2018 | Khoury et al. |
| 2018/0211670 | A1 * | 7/2018 | Gorodetski ............. G10L 17/04 |
| 2018/0342240 | A1 * | 11/2018 | Shellef .................... G10L 25/84 |
| 2020/0125795 | A1 * | 4/2020 | Zimmerman ......... G06F 40/186 |
| 2020/0219492 | A1 * | 7/2020 | Apsingekar .............. G06N 7/01 |
| 2020/0312337 | A1 | 10/2020 | Stafylakis et al. |
| 2021/0272571 | A1 * | 9/2021 | Balasubramaniam .. G10L 15/02 |

(Continued)

OTHER PUBLICATIONS

Khare, A., Han, E., Yang, Y., & Stolcke, A. (May 2022). ASR-aware end-to-end neural diarization. In ICASSP 2022-2022 IEEE International Conference on Acoustics, Speech and Signal Processing (ICASSP) (pp. 8092-8096). IEEE. (Year: 2022).*

(Continued)

*Primary Examiner* — Bhavesh M Mehta
*Assistant Examiner* — Philip H Lam
(74) *Attorney, Agent, or Firm* — Nicholson De Vos Webster & Elliott LLP

(57) ABSTRACT

Techniques for performing speaker error correction are described. In some examples, speaker error correction is a post-processing task aligned predicted words and predicted one or more speaker identities, wherein the post-processing at least includes: performing predicted speaker error correction on the aligned predicted words and predicted one or more speaker identities to generate a first corrected set of speaker error corrections of the one or more speaker identifiers.

20 Claims, 15 Drawing Sheets

(56) References Cited

U.S. PATENT DOCUMENTS

| | | | |
|---|---|---|---|
| 2021/0375289 A1 | 12/2021 | Zhu et al. | |
| 2022/0199091 A1 | 6/2022 | Kanda et al. | |
| 2022/0199094 A1* | 6/2022 | El Shafey | G06N 3/044 |
| 2022/0254351 A1* | 8/2022 | Jung | G06F 40/216 |
| 2022/0335947 A1 | 10/2022 | Li et al. | |
| 2023/0019978 A1* | 1/2023 | Raghunathan | G10L 15/063 |
| 2023/0115212 A1* | 4/2023 | Salamon | G10H 1/0008 84/602 |
| 2023/0352009 A1 | 11/2023 | Behre et al. | |
| 2024/0127820 A1 | 4/2024 | Salamon et al. | |
| 2024/0177730 A1 | 5/2024 | Dougherty et al. | |

OTHER PUBLICATIONS

López-Cózar, R., & Callejas, Z. (2008). ASR post-correction for spoken dialogue systems based on semantic, syntactic, lexical and contextual information. Speech Communication, 50(8-9), 745-766. (Year: 2008).*

Park, T. J., & Georgiou, P. (2018). Multimodal speaker segmentation and diarization using lexical and acoustic cues via sequence to sequence neural networks. arXiv preprint arXiv:1805.10731. (Year: 2018).*

Park, T. J., Han, K. J., Huang, J., He, X., Zhou, B., Georgiou, P., & Narayanan, S. (2020). Speaker diarization with lexical information. arXiv preprint arXiv:2004.06756. (Year: 2020).*

Xia, W., Lu, H., Wang, Q., Tripathi, A., Huang, Y., Moreno, I. L., & Sak, H. (May 2022). Turn-to-diarize: Online speaker diarization constrained by transformer transducer speaker turn detection. In ICASSP 2022-2022 IEEE International Conference on Acoustics, Speech and Signal Processing (ICASSP) (Year: 2022).*

Mao, H. H., Li, S., McAuley, J., & Cottrell, G. (2020). Speech recognition and multi-speaker diarization of long conversations. arXiv preprint arXiv:2005.08072. (Year: 2020).*

Non-Final Office Action, U.S. Appl. No. 18/331,517, Jul. 15, 2025, 13 pages.

Notice of Allowance, U.S. Appl. No. 18/331,517, Oct. 29, 2025, 16 pages.

* cited by examiner

WRITTEN TEXT, PLUS SPEAKER
IDENTIFIERS (AND IN SOME
EXAMPLES A PERPLEXITY
SCORE)

POST-PROCESSING 215

OTHER POST-PROCESSING 219

MERGER 218

WORD OUTPUT (RE-)ALIGNED TO
PREDICTED SPEAKERS

ITN, PUNCTUATION, AND/OR
CASING 216

SPEAKER ERROR CORRECTION 217

WORD OUTPUT ALIGNED TO
PREDICTED SPEAKERS 213

RECONCILIATION 211

WORD OUTPUT
207

ONE OR MORE PREDICTED
SETS OF SPEAKERS
AND/OR FEATURES
209

ASR 203

SPEAKER DIARIZATION
205

AUDIO INPUT
201

TRANSCRIPTION SERVICE 110

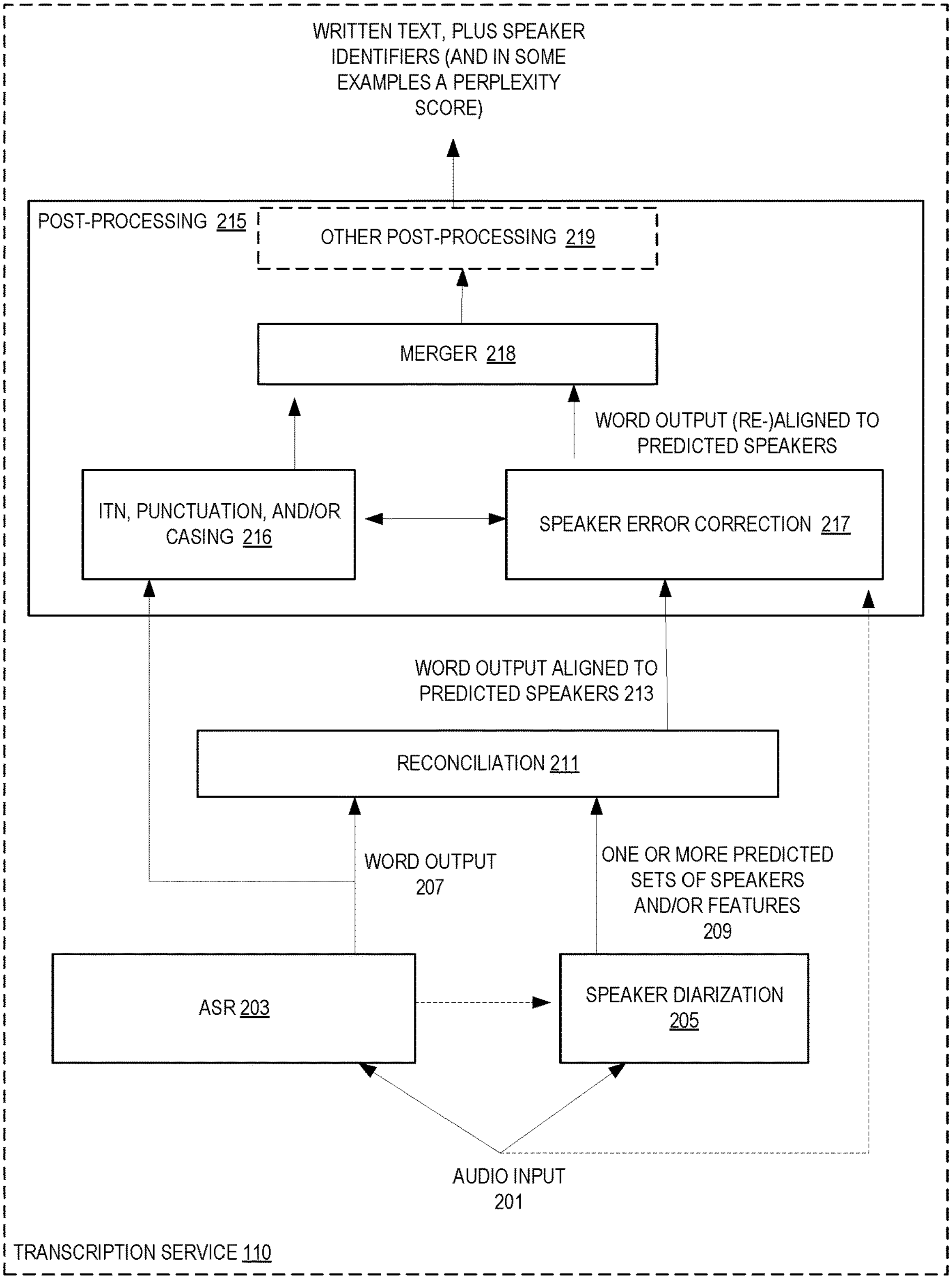

FIG. 2

WORDS
411

CORRECTED SPEAKER IDS
409

SPEAKER ERROR CORRECTION 217

LEXICAL CORRECTOR 400

ENCODER 403

TOKEN LEVEL
SPEAKER ID MAPPING
407

WORD EMBEDDINGS
405

PRE-TRAINED LANGUAGE MODEL 401

WORD OUTPUT ALIGNED TO
PREDICTED SPEAKERS 213

TRAIN A TRANSCRIPTION SYSTEM 602

RECEIVE REQUEST TO TRANSCRIBE AUDIO 604

TRANSCRIBE THE AUDIO ACCORDING TO THE REQUEST 606

PREDICT WORDS IN THE AUDIO 608

PREDICT ONE OR MORE SPEAKERS IN THE AUDIO 610

RECONCILE THE WORDS WITH THE PREDICTED ONE OR MORE SPEAKERS 612

PERFORM POST PROCESSING 613

PERFORM SPEAKER ERROR CORRECTION 614

PERFORM LEXICAL ERROR CORRECTION 616

GENERATE (SUB-)WORD EMBEDDINGS 618

PREDICT A (FIRST) SET OF CORRECTED SPEAKER IDENTITIES PER (SUB-)WORD 620

PREDICT AUDIO FEATURES 622

PREDICT A SECOND SET OF CORRECTED SPEAKER IDENTITIES 624

PERFORM OTHER POST PROCESSING 626

OUTPUT THE TRANSCRIBED AUDIO 628

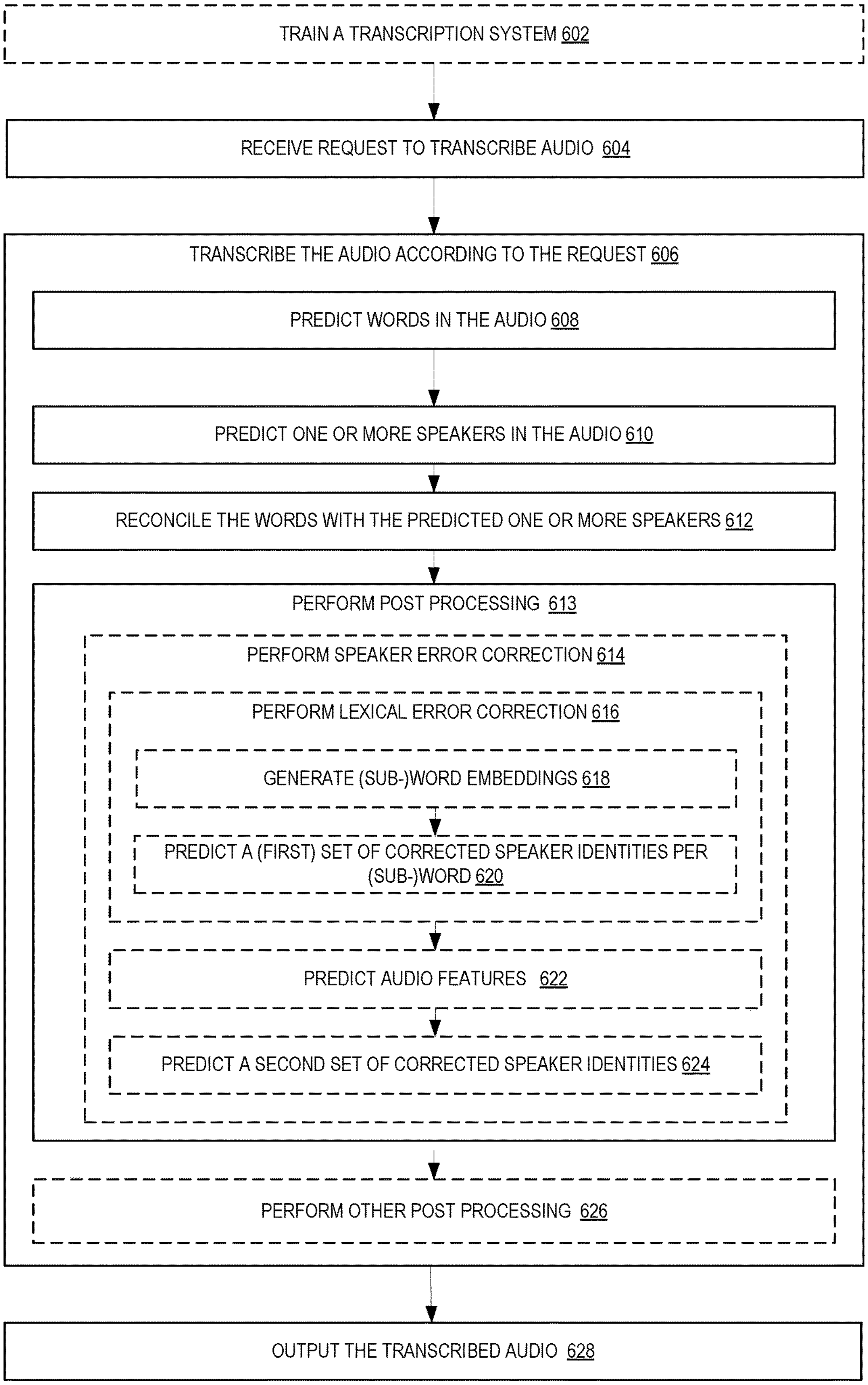

FIG. 6

TRAIN A TRANSCRIPTION SYSTEM 902

RECEIVE REQUEST TO TRANSCRIBE AUDIO 904

TRANSCRIBE THE AUDIO ACCORDING TO THE REQUEST 906

PREDICT WORDS IN THE AUDIO 908

PREDICT ONE OR MORE SPEAKERS IN THE AUDIO 910

RECONCILE THE WORDS WITH THE PREDICTED ONE OR MORE SPEAKERS 912

PERFORM POST PROCESSING 913

PERFORM JOINT SPEAKER ERROR CORRECTION AND AT LEAST ITN 914

PREDICT WORD AND SPEAKER CONTEXTUAL FEATURES USING AN ENCODER 916

PREDICT AT LEAST ITN CORRECTED TEXT AND SPEAKER IDENTIFIERS USING THE PREDICTED WORD AND SPEAKER CONTEXTUAL FEATURES AND A TOKENIZED INPUT SEQUENCE USING AN AUTOREGRESSIVE DECODER 918

PERFORM OTHER POST PROCESSING 920

OUTPUT THE TRANSCRIBED AUDIO 922

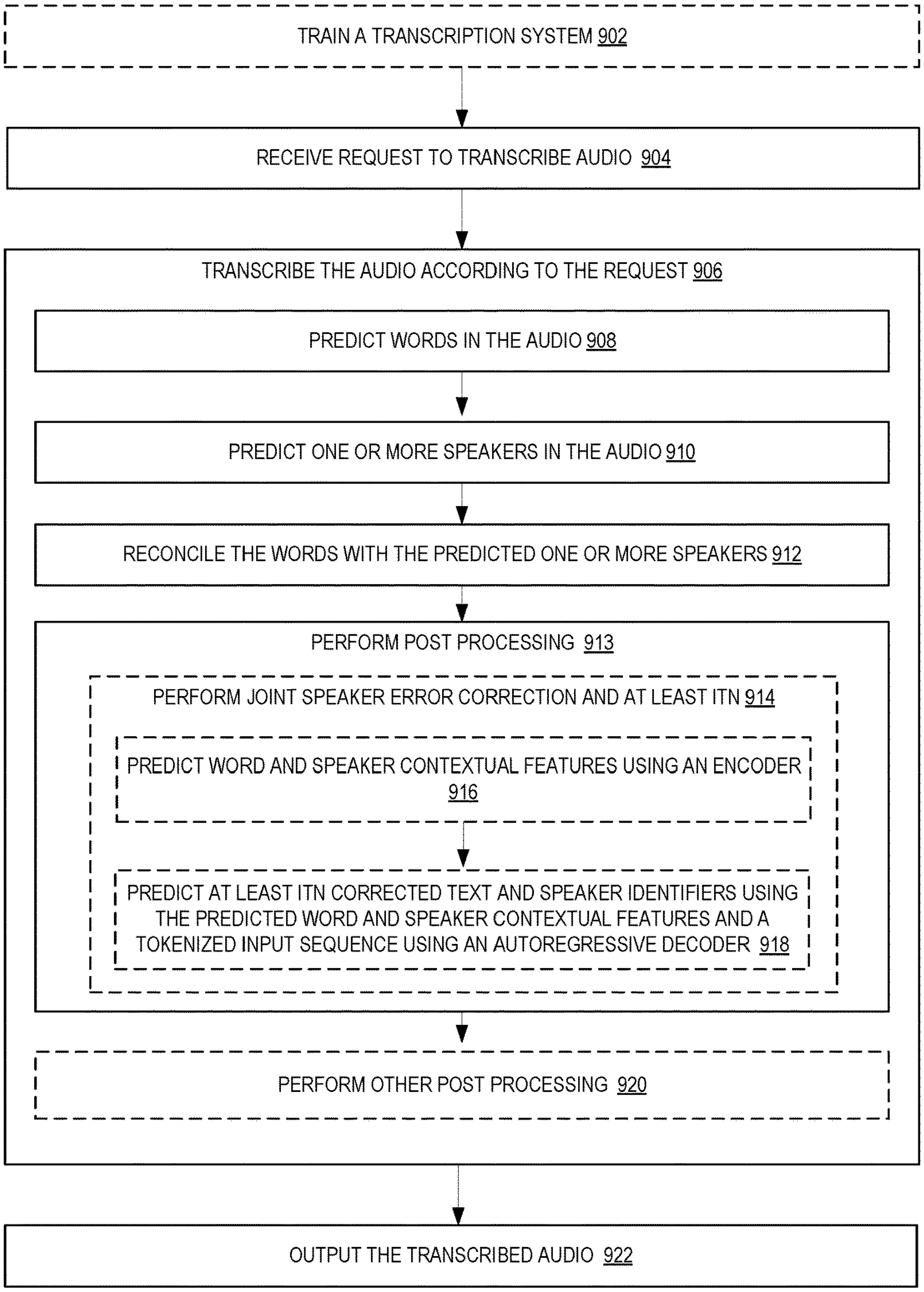

*FIG. 9*

TRAIN A TRANSCRIPTION SYSTEM 1202

RECEIVE REQUEST TO TRANSCRIBE AUDIO 1204

TRANSCRIBE THE AUDIO ACCORDING TO THE REQUEST 1206

PREDICT WORDS IN THE AUDIO 1208

PREDICT ONE OR MORE SPEAKERS IN THE AUDIO 1210

RECONCILE THE WORDS WITH THE PREDICTED ONE OR MORE SPEAKERS 1212

PERFORM POST PROCESSING 1213

PERFORM JOINT SPEAKER ERROR CORRECTION AND AT LEAST ITN 1214

GENERATE (SUB-)WORD EMBEDDINGS 1216

PREDICT A SET OF CORRECTED SPEAKER IDENTITIES PER (SUB-)WORD 1218

PREDICT AT LEAST ITN CORRECTED TEXT AND CORRECTED SPEAKER IDENTIFIERS USING THE PREDICTED SET OF CORRECTED SPEAKER IDENTITIES AND WORD EMBEDDINGS USING A NON-AUTOREGRESSIVE DECODER 1220

PERFORM OTHER POST PROCESSING 1222

OUTPUT THE TRANSCRIBED AUDIO 1224

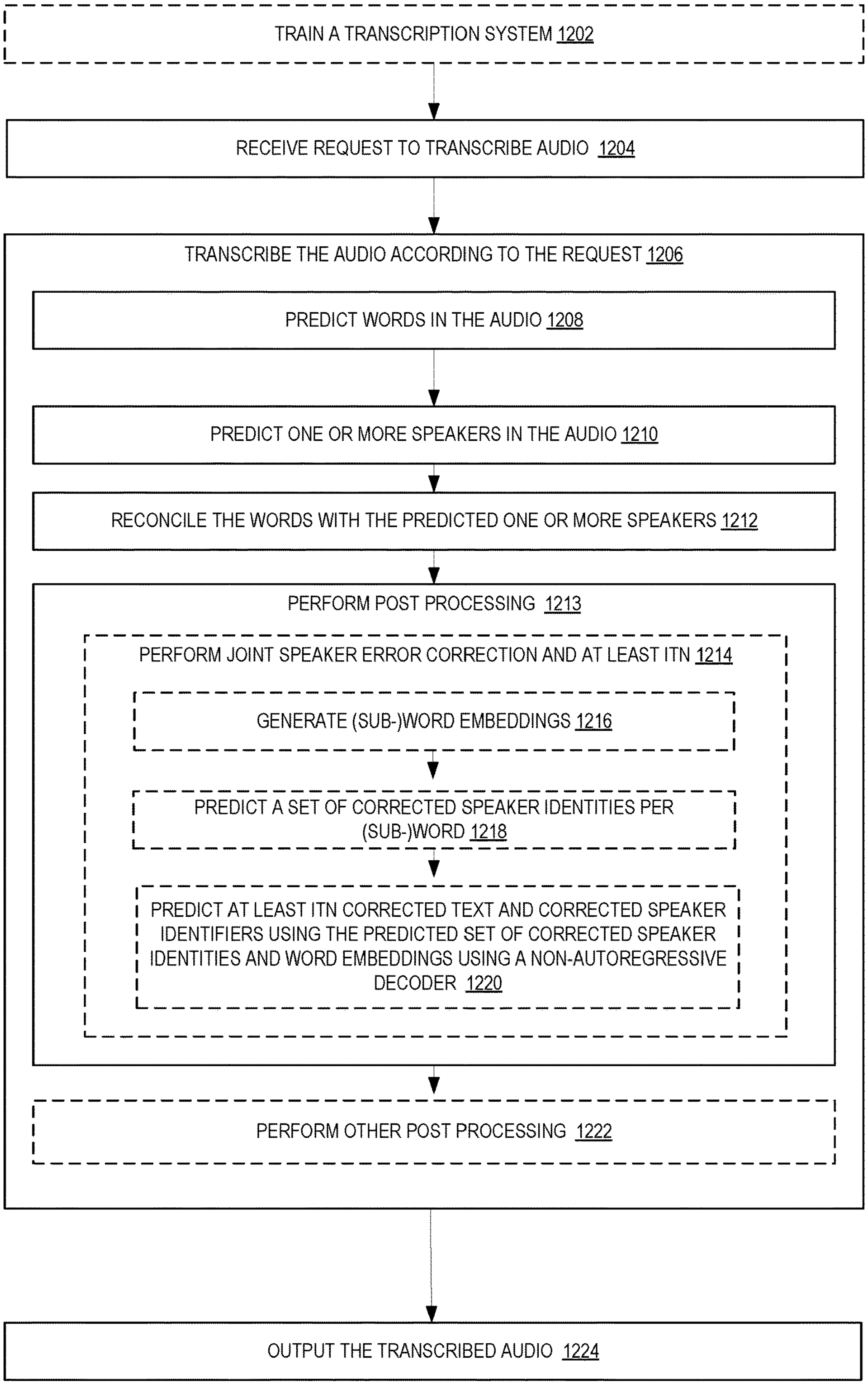

*FIG. 12*

JOINT ASR AND SPEAKER ERROR CORRECTION POST-PROCESSING

BACKGROUND

Computer-implemented speech recognition allows for a computing device to take in audio data and generate text representing the audio data. Many different algorithmic approaches and computation techniques are used to turn speech into text. In some instances, speech recognition is used as a part of a speech transcription system that provides text from audio.

A model used in speech recognition is the hidden Markov model (HMM). HMMs incorporate hidden events, such as part-of-speech tags, into a probabilistic model. HMMs are utilized as sequence models within speech recognition and assign labels to each unit in a sequence. These labels create a mapping with the provided input, allowing an HMM to determine the most appropriate label sequence.

A N-gram language model (LM) assigns probabilities to sentences or phrases when an N-gram is sequence of N-words. Neural networks are also used for speech recognition, such as convolution neural networks (CNNs), recurrent neural networks (RNNs) such as Long Short Term Memory (LSTM) models, Transformer-based models (e.g., Wav2Vec, etc.), etc.

BRIEF DESCRIPTION OF DRAWINGS

Various examples in accordance with the present disclosure will be described with reference to the drawings, in which:

FIG. 2 illustrates examples of a transcription service.

FIG. 6 is a flow diagram illustrating operations of a method for transcribing audio according to some examples.

FIG. 9 is a flow diagram illustrating operations of a method for transcribing audio according to some examples.

FIG. 12 is a flow diagram illustrating operations of a method for transcribing audio according to some examples.

DETAILED DESCRIPTION

Figure 1:
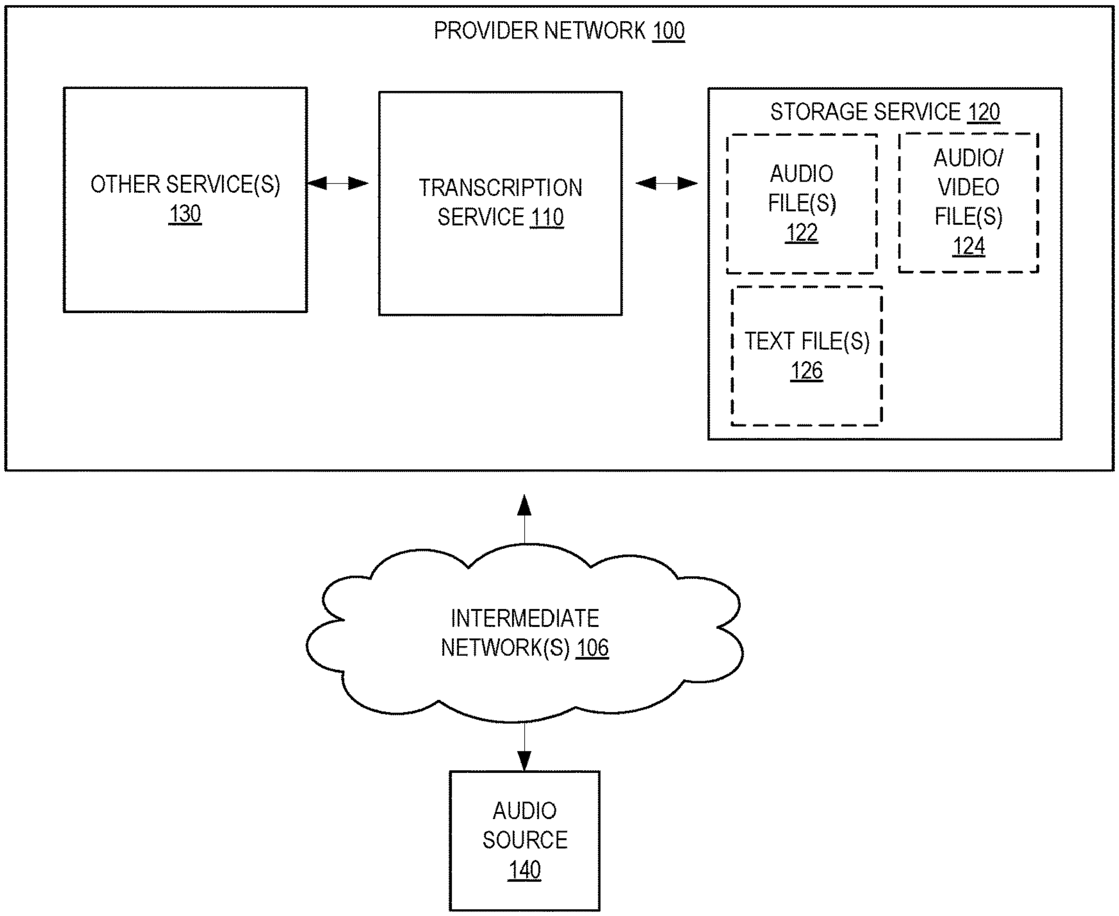
FIG. 1 illustrates examples involving the use of a transcription service.

The present disclosure relates to methods, apparatus, systems, and non-transitory computer-readable storage media for correcting speaker identifiers.

Speech transcription systems have advanced significantly, but even with these advances, these systems have difficulties understanding natural conversations with multiple speakers such as in broadcast interviews, meetings, telephone calls, videos, or medical recordings. Further, while some speech transcription systems also provide an indication of who was speaking a particular word or phrase, there can be errors in aligning a speaker in a multi-speaker audio with the predicted text.

In some speech transcription systems, multiple operations are performed to generate a first pass of word-to-speaker alignment. The words in the audio are transcribed using an automatic speed recognition (ASR) system. Additionally, a prediction is made of "who spoke when" using a speaker diarization (SD) system. SD assigns a speaker label to each transcribed speaker turn and has widespread applications in generating meeting/interview transcripts, medical notes, automated subtitling and dubbing, downstream speaker analytics, among others.

In some examples, SD systems perform several tasks including: 1) segmenting the input audio into speech segments using a voice activity detector (VAD), 2) generating speaker segments from the speech segments by either using a uniform window size or by detecting speaker turns, 3) extracting speaker embeddings for each of the speaker segments, and 4) clustering the resulting speaker embeddings using clustering algorithms. In those systems, the SD system typically uses only acoustic information to identify the speakers in the audio stream. This approach can lead to speaker errors, especially around speaker turns and regions of speaker overlap. This can happen in uniform speaker segmentation as long segments very likely contain speaker turn boundaries, while short segments carry insufficient speaker information.

The outputs of the ASR and SD are reconciled using windows or speaker turns. In addition to the SD errors, speakers can be attributed to the wrong words in the SD-ASR reconciliation phase due to errors in ASR word timings. Reconciliation errors can also occur in regions of speech overlap as SD can identify one of the speakers while ASR can identify words corresponding to a different speaker.

Detailed herein are examples that use a "second-pass" speaker error correction system using at least lexical information. Lexical information can contain complementary information, which can be very useful in accurately predicting speaker turns. For instance, analyzing only the written transcript of a conversation, such as "how are you i am good", enables an inference that there is likely a speaker change between the utterances "how are you" and "i am good." In some examples, the second-pass speaker systems leverages the power of LMs.

In some examples, a Speaker Error Correction (SEC) component acts as a "second-pass" speaker error correction system corrects speaker identification errors at the word level without modifying any underlying ASR or the acoustic SD system. In some examples, the SEC component uses a pre-trained LM (e.g., Bidirectional Encoder Representations from Transformers (BERT), Robustly optimized BERT pre-training approach (ROBERTA), XLnet, generative pre-trained Transformer (GPT), large language model Meta AI (LLAMA), other sequence-to-sequence models, etc.) to infuse lexical knowledge to correct speaker errors while also leveraging speaker scores from the SD system to prevent over-corrections. Using LMs also significantly reduces the amount of speaker-labelled text data needed to train the system. The SEC component follows the reconciliation stage and takes in at least two streams of inputs: acoustic features from the SD and lexical features from the ASR.

FIG. 1 illustrates examples involving the use of a transcription service. As illustrated, a transcription service 110 of a provider network 100 transcribes audio into text in response to a request. In some examples, the output of the transcription service 110 is one or more of: raw text, normalized text, punctuated text, formatted text (e.g., transcribe the use of digits instead of words), time stamps (e.g., per word, per speaker turn, etc.), speaker identification(s), channel identification, etc. In some examples, the transcription service 110 uses custom language models and/or a custom vocabulary (e.g., domain-specific models and/or vocabulary). In some examples, the transcription service 110 filters certain words (e.g., profane or otherwise offensive words), redacts personally identifiable information (PII), etc. The transcription service 110 utilizes a SEC component to correct speaker identification errors that may be introduced by simple reconciliation of ASR and SD.

In some examples, the provider network 100 supports a storage service 120. Audio files 122 and/or audio/video files 124 to be transcribed may be stored using this service. The output of the transcription service 110 (e.g., a text file 126) may be stored using the service.

One or more other services 130 may interact with either of the above services. For example, a service that provides audio/video files to a user (e.g., a streaming service) may use the transcription service 110 to generate closed captions. A medical records service may use the transcription service 110 to transcribe patient/doctor notes. A call center service may use the transcribe service to transcribe calls to be used to improve productivity and/or responses for customer calls.

In some examples, an external audio source 140 (e.g., an audio file, audio/video file, an audio stream, an audio/video stream, etc.) may provide the audio to be transcribed.

The provider network 100 (or, "cloud" provider network) provides users with the ability to use one or more of a variety of types of computing-related resources such as compute resources (e.g., executing virtual machine (VM) instances and/or containers, executing batch jobs, executing code without provisioning servers), data/storage resources (e.g., object storage, block-level storage, data archival storage, databases and database tables, etc.), network-related resources (e.g., configuring virtual networks including groups of compute resources, content delivery networks (CDNs), Domain Name Service (DNS)), application resources (e.g., databases, application build/deployment services), access policies or roles, identity policies or roles, machine images, routers and other data processing resources, etc. These and other computing resources can be provided as services, such as a hardware virtualization service that can execute compute instances, a storage service that can store data objects, etc. The users (or "customers") of provider networks 100 can use one or more user accounts that are associated with a customer account, though these terms can be used somewhat interchangeably depending upon the context of use. Users can interact with a provider network 100 across one or more intermediate networks 106 (e.g., the internet) via one or more interface(s), such as through use of application programming interface (API) calls, via a console implemented as a website or application, etc. An API refers to an interface and/or communication protocol between a client and a server, such that if the client makes a request in a predefined format, the client should receive a response in a specific format or initiate a defined action. In the cloud provider network context, APIs provide a gateway for customers to access cloud infrastructure by allowing customers to obtain data from or cause actions within the cloud provider network, enabling the development of applications that interact with resources and services hosted in the cloud provider network. APIs can also enable different services of the cloud provider network to exchange data with one another. The interface(s) can be part of, or serve as a front-end to, a control plane of the provider network 100 that includes "backend" services supporting and enabling the services that can be more directly offered to customers.

For example, a cloud provider network (or just "cloud") typically refers to a large pool of accessible virtualized computing resources (such as compute, storage, and networking resources, applications, and services). A cloud can provide convenient, on-demand network access to a shared pool of configurable computing resources that can be programmatically provisioned and released in response to customer commands. These resources can be dynamically provisioned and reconfigured to adjust to variable load. Cloud computing can thus be considered as both the applications delivered as services over a publicly accessible network (e.g., the Internet, a cellular communication network) and the hardware and software in cloud provider data centers that provide those services.

A cloud provider network can be formed as a number of regions, where a region is a geographical area in which the cloud provider clusters data centers. Each region includes multiple (e.g., two or more) availability zones (AZs) connected to one another via a private high-speed network, for example a fiber communication connection. An AZ (also known as a "zone") provides an isolated failure domain including one or more data center facilities with separate power, separate networking, and separate cooling from those in another AZ. A data center refers to a physical building or enclosure that houses and provides power and cooling to servers of the cloud provider network. Preferably, Azs within a region are positioned far enough away from one another so that a natural disaster (or other failure-inducing event) should not affect or take more than one AZ offline at the same time.

Users can connect to an AZ of the cloud provider network via a publicly accessible network (e.g., the Internet, a cellular communication network), e.g., by way of a transit center (TC). TCs are the primary backbone locations linking users to the cloud provider network and can be collocated at other network provider facilities (e.g., Internet service providers (ISPs), telecommunications providers) and securely connected (e.g., via a VPN or direct connection) to the Azs. Each region can operate two or more TCs for redundancy. Regions are connected to a global network which includes private networking infrastructure (e.g., fiber connections controlled by the cloud provider) connecting each region to at least one other region. The cloud provider network can deliver content from points of presence (or "POPs") outside of, but networked with, these regions by way of edge locations and regional edge cache servers. This compartmentalization and geographic distribution of computing hardware enables the cloud provider network to provide low-latency resource access to users on a global scale with a high degree of fault tolerance and stability.

To provide these and other computing resource services, provider networks 100 often rely upon virtualization techniques. For example, virtualization technologies can provide users the ability to control or use compute resources (e.g., a "compute instance," such as a VM using a guest operating system (O/S) that operates using a hypervisor that might or might not further operate on top of an underlying host O/S, a container that might or might not operate in a VM, a compute instance that can execute on "bare metal" hardware without an underlying hypervisor), where one or multiple compute resources can be implemented using a single electronic device. Thus, a user can directly use a compute resource (e.g., provided by a hardware virtualization service) hosted by the provider network to perform a variety of computing tasks. Additionally, or alternatively, a user can indirectly use a compute resource by submitting code to be executed by the provider network (e.g., via an on-demand code execution service), which in turn uses one or more compute resources to execute the code typically without the user having any control of or knowledge of the underlying compute instance(s) involved.

As described herein, one type of service that a provider network may provide may be referred to as a "managed compute service" that executes code or provides computing resources for its users in a managed configuration. Examples of managed compute services include, for example, an on-demand code execution service, a hardware virtualization service, a container service, or the like.

FIG. 2 illustrates examples of a transcription service. An ASR component 203 generates a word output 207 from an audio input 201. Examples of audio input 201 include, but are not limited to: audio files, streaming audio, audio/video files, streaming audio/video, etc. The audio input 201 is stored by the storage service 120 in some examples.

In some examples, the ASR component 203 is a machine learning model. Examples ASR models include, but are not limited to: Wav2Vec variants, Jasper variants, Transformer-based (e.g., Conformer-based variants, Whisper variants, etc.), Long Short-Term Memory (LSTM)-based, Connectionist Temporal Classification (CTC)-based, hidden unit BERT (HuBERT), etc. The ASR component 203 outputs predicted words of the audio input 201.

The audio input 201 is also supplied to a speaker diarization component 205 that predicts (detects) a speaker from the audio input 201 and/or determines audio features and outputs speaker embeddings and/or feature embeddings. In some examples, as noted above, the SD component 205 performs a plurality of tasks such as segmenting the input audio into speech segments using a voice activity detector (VAD), generating speaker segments from the speech segments (e.g., by using a uniform window size, by detecting speaker turns, etc.), extracting speaker embeddings for each of the speaker segments, and clustering the resulting speaker embeddings using a clustering algorithms (e.g., spectral clustering, agglomerative hierarchical clustering, etc.). These tasks rely only on acoustic information, in some examples, and can thus lead to speaker errors. The overall output 209 at least includes speaker labels with time boundaries. In some examples, other features are also output.

In some examples, the segmenting is performed using an LSTM-based speech detector. In some examples, speaker embedding are extracted using an LSTM model with a hidden state of the LSTM model being the speaker embedding. In some examples, speaker segments are calculated by detecting a speaker change from using a distance calculation (e.g., a cosine distance is computed between adjacent embedding vectors in the speech segments) and when the distance is above a threshold, a speaker change is considered to have occurred.

The output of the SD component 205 and ASR component 203 are reconciled using a reconciliation component 211 to assign a speaker label to each transcribed speaker turn. The SD component 205 provides speaker turns with time boundaries and these labels are mapped to recognized words using the associated word boundaries from the ASR component 203. When the speaker turn boundary falls in the middle of a word, the word is assigned to the speaker with the largest overlap with the word. The output 213 of the reconciliation component 211 includes words in the audio and speaker labels $$\{S_i\}_{i=1}^N,\ S_i \in \mathbb{R}^{1\times K}$$

for every word $$\{W_i\}_{i=1}^N,$$

where N is the number of words in the sequence and K is the number of speakers the speaker error corrector 217 component is trained to handle. In some examples, there are different speaker error correctors to use based on the number of predicted speakers.

Post-processing is performed on the output of the ASR component 203 and/or the output of the reconciliation component 211 using post-processing component(s) 215. In some examples, the output of the ASR component 203 is converted into a written form using inverse text normalization (ITN), casing, and/or punction component 216. In some examples, ITN is performed using a weighted finite state transducer (WEST). In some examples, punctuation is added to the output of the ASR component 203 and/or the ITN output. In some examples, a Transformer-based model is used for punctuation. In some examples, the punctuation model is language specific (e.g., English, French, etc.).

Figure 3:
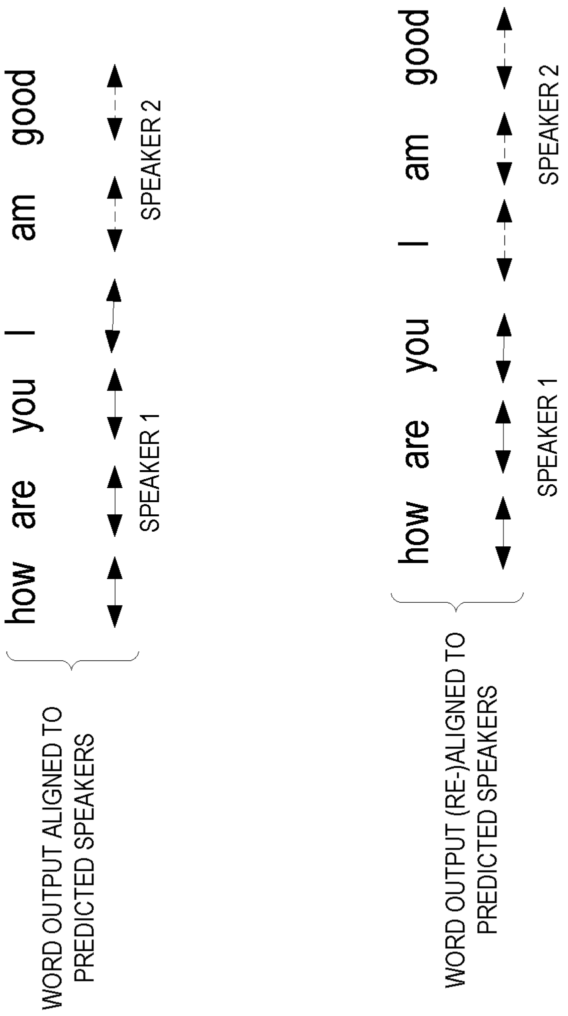
FIG. 3 illustrates examples of an output after reconciliation for first pass from a SD and a second pass from a speaker error corrector.

A SEC component 217 performs the "second pass" on the reconciled output to correct for speaker errors at the word level. FIG. 3 illustrates examples of an output after reconciliation for first pass from a SD and a second pass from a speaker error corrector. In this illustration, the predicted text out of ASR is "how are you I am good." As shown, the word aligned output from reconciliation 213 found that there were two speakers, but the "I" was aligned with speaker 1. A human would understand that the "I" belongs to a second speaker. The output of the second pass properly aligns the "I".

In some examples, the output of the SEC component 217 and ITN and/or punctuation is merged using merger 218. As such, the output will have speaker labels, punctuation, etc. In some examples, time stamps of the text are also included. In some examples, if a speaker's name is known (e.g., his/her voice recognized), the name will be used as a speaker label.

Figure 4:
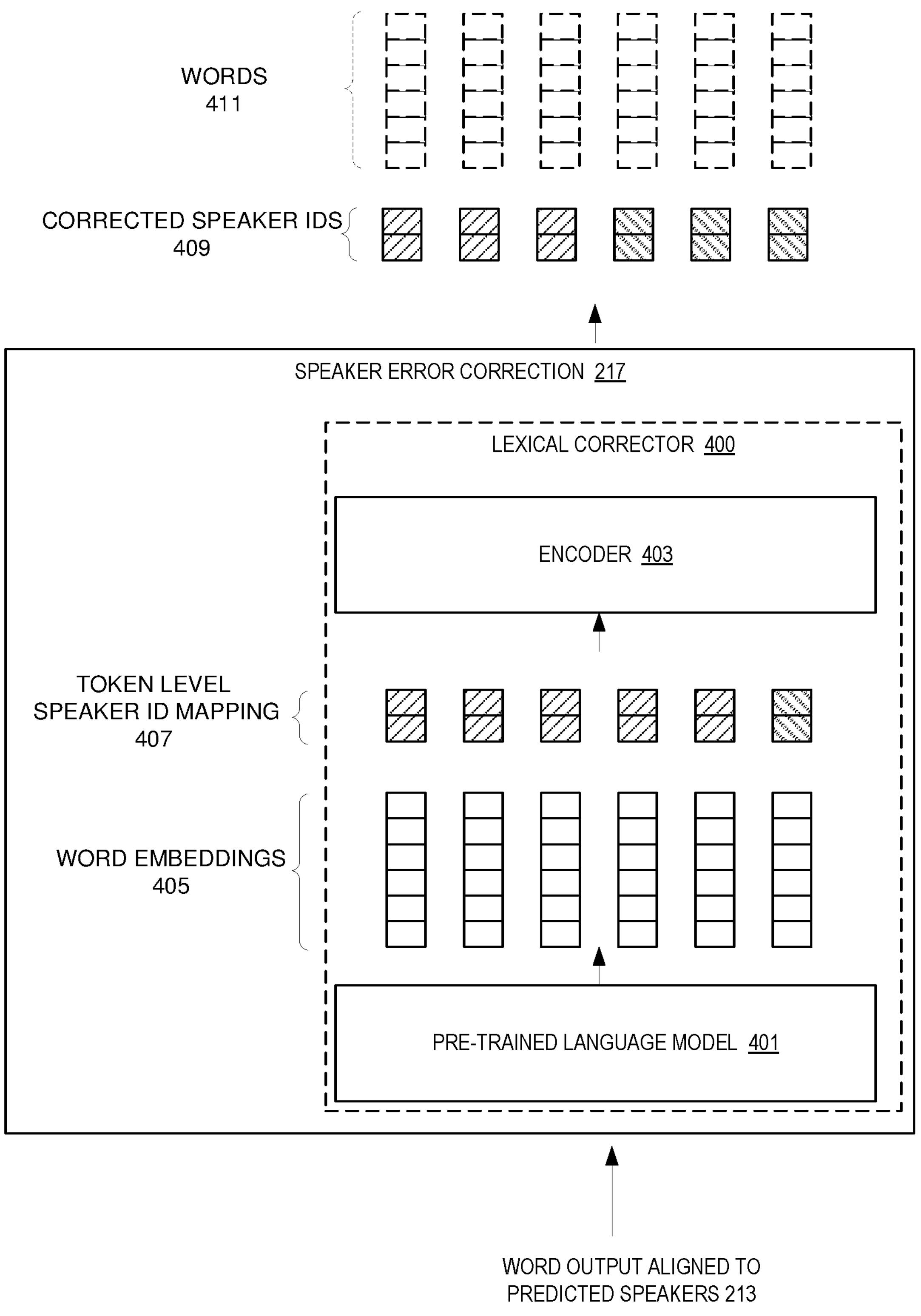
FIG. 4 illustrates examples of a speaker error corrector.

FIG. 4 illustrates examples of a speaker error corrector such as the SEC component 217. Note that in some examples, the correction is only a lexical correction performed by lexical corrector 400. A pre-trained language model (LM) 401 takes in the word output $W_i$ that is aligned to detected speakers (e.g., the reconciliation output 213) to generate contextual word embeddings 405

$$\text{(e.g., } \{E_j\}_{j=1}^M,\ E_i \in \mathbb{R}^{1\times W}$$

where M is the number of tokens in the word sequence and W is the word embedding dimension). In some examples, the word output Weis tokenized prior to the LM 401. The word level speaker labels $S_i$ are mapped to a token level by mapping a speaker ID corresponding to the word to its first token when the word has more than two tokens and a "don't care" token is assigned to any subsequent tokens of the word. This is shown as token level speaker ID mapping 407.

In some examples, the token level embeddings $E_j$ are concatenated (or otherwise combined) with the speaker IDs $S_j$ to generate fused features to be input into an encoder 403. In some examples, the encoder 403 is Transformer-based. The encoder 403 generates corrected speaker ID mappings 409.

The SEC component 217 of FIG. 4 only looks at lexical features in some examples. However, lexical features can have complementary information in the form of acoustic features which can be leveraged to correct some of the errors from a naïve reconciliation of ASR and SD as, in some examples, lexical features alone do not accurately predict speaker labels. In particular, due to reliance on only audio, VAD false alarms, and/or bad ASR word timing, words around speaker turns may be misaligned to the wrong speakers. Linguistic cues can provide important complementary information which can be useful in rectifying such errors.

In some examples, a second pass diarization corrector leverages both lexical and audio information to correct errors produced by the audio-based diarizer. This may help prevent the lexical corrector 400 from over-correcting and increasing turn boundary errors.

Figure 5:
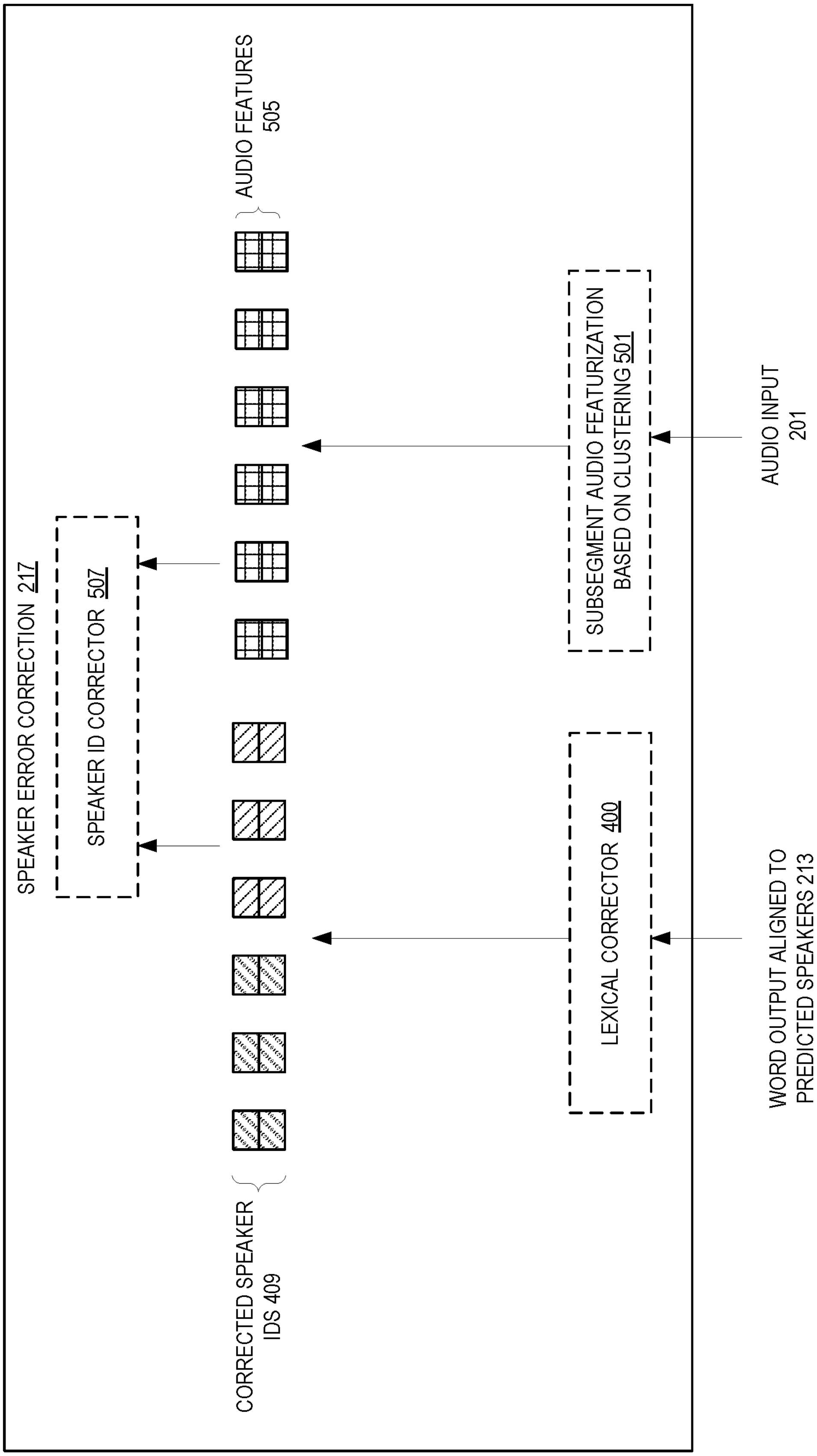
FIG. 5 illustrates examples of a speaker error corrector.

FIG. 5 illustrates examples of a speaker error corrector such as speaker error correction component 217 that utilizes a second pass diarization corrector. In this example, lexical and audio features are used to correct speaker IDS. Lexical correction is performed by lexical corrector 400 on an input word output aligned to detected speakers to generate corrected speaker ID mappings 409.

Audio input 201 is fed into an audio featurization a sub-segmenter 501 to generate word-aligned sub-segments of audio features 505. In some examples, the sub-segmentation is based on clustering. The corrected, lexical-based speaker ID mappings 409 and audio features 505 are fed into a speaker ID corrector 507 to generate corrected speaker IDs. In some examples, the speaker ID corrector 507 is a Transformer-based encoder.

In some examples, during inference, the speaker error correction component 217 performs error correction on sliding windows of a fixed number of transcribed words. In some examples, the size of the sliding windows (in words) is selectable. In some examples, when the speaker error correction component 217 (e.g., the lexical corrector 400) has been trained for a set number of speakers (e.g., K=2), when the number of speakers is greater than that size (e.g., K>2), only the first pass of speaker IDs are used (thereby bypassing) the encoder of the speaker error correction component 217 or the speaker error correction component 217.

In some examples, the speaker error correction only corrects speaker identifiers that have been generated by the SD 205, which is generally based only on acoustic features. In some examples, the SD 205 clusters speaker embeddings extracted from sub-segments and the number of speaker clusters is determined by a maximum eigen gap or other such cluster heuristics which are based on acoustic information. Due to the reliance on purely acoustic features, the heuristics for speaker counting can be erroneous in the case of similar sounding speakers, background noise, channel artifacts, etc.

In some examples, the SD 205 utilizes lexical content to determine sets of speaker identities (labels) based on clustering and outputs a plurality of predicted sets of speakers and/or features 209. Clustering variants to use may include one or more of agglomerative, spectral, etc. When multiple clusters are predicted, the reconciliation component 211 outputs a plurality of speaker aligned words. Examples are reconciliation outputs are shown below where clusters aligns with the number of predicted speakers:

Clustering variant 1 (#clusters=2): Where do <spk1> you live I <spk2> live in New York <spk1>

Clustering variant 1 (#clusters=3): Where do you <spk1> live I <spk2> live in New York <spk3>

Clustering variant 2 (#clusters=2) Where do you live <spk1> I live in New York <spk2>

Clustering variant 2 (#clusters=3): Where do <spk1> you live I live <spk2> in New York <spk3>

In some examples, other processing 219 performs one or more of ITN, casing, punctuation, and/or generating speaker perplexity values. Speaker perplexity values being generated when the speaker error correction 217 produces multiple outputs from the multiple outputs of the reconciliation 211. Perplexity is a statistical measure of how confidently a model predicts a sample. The lower the perplexity, the higher probability of the sequence of words. Speaker perplexity is determined from a language model (e.g., BERT, GPT, LLAMA, BART, T5 etc.) in some examples. In the above examples of reconciliation outputs are, the third example has a probability of the sequence of words in the individual speaker turns that is greater than the probability of the word sequences in individual speaker turns of the other variants. The speaker perplexity may be used to determine which of the multiple outputs of the SEC 217 to use.

In other examples, as a part of reconciliation 211, speaker perplexity is calculated and used to determine the number of clusters and/or clustering approach to use. In these examples, the best clustering variant is provided to the SEC 217.

FIG. 6 is a flow diagram illustrating operations of a method for transcribing audio according to some examples. Some or all of the operations (or other processes described herein, or variations, and/or combinations thereof) are performed under the control of one or more computer systems configured with executable instructions, and are implemented as code (e.g., executable instructions, one or more computer programs, or one or more applications) executing collectively on one or more processors. The code is stored on a computer-readable storage medium, for example, in the form of a computer program comprising instructions executable by one or more processors. The computer-readable storage medium is non-transitory. In some examples, one or more (or all) of the operations are performed by the transcription service 110 of the other figures.

In some examples, a transcription system is trained at 602. In some examples, this training includes training of one or more of an ASR, a SD, and/or a speaker error corrector. The training may include the re-training of one or more of the models for those components.

A request to transcribe audio is received at 604. The request includes one or more of: an indication of a source of the audio (e.g., a location of a file, a location of a stream, etc.), an indication of a language of the audio, an indication of a location to store the transcription, an indication of where to provide the transcription, an indication of a model to use for ASR, SD, etc., The audio is transcribed according to the request using a SEC at 606. The transcription may include one or more acts. The words in the audio are predicted using ASR at 608. For example, an ASR model is applied to the audio. Note that in some examples a particular ASR model is used if so indicated by the request.

One or more speakers in the audio are predicted at 610. For example, SD is performed. In some examples, features are also determined.

The words of the audio are reconciled with the predicted one or more speakers to generate word output that is aligned to the predicted speakers at 612.

Post-processing is then performed at 613. In some examples, when there is only one predicted speaker, other non-SEC post-processing is performed such as ITN and punctuation inclusion at 626. In some examples, when there are more predicted speakers than the SEC is trained to handle, other non-SEC post-processing is performed at 626.

In some examples, speaker error correction is performed on the word output that is aligned to the predicted speakers at 614.

Lexical error correction is performed on the word output that is aligned to the predicted speakers at 616. In some examples, the lexical error correction utilizes a pre-trained language model to generate word or sub-word embeddings at 618 which are then mapped to speaker identifiers at 620. The (sub-) word embeddings and mapped speaker identifiers are provided to an encoder which predicts corrected speaker IDs for the (sub-) word embeddings at 620. In some examples, the corrected speaker IDs are a first set of corrected speaker IDs.

In some examples, audio features of the audio are predicted at 622. In some examples, these audio features are a selected subsegments of predicted audio features. The selection may be done by calculating distances for the speakers to one or more clusters and making a selection thereof.

In some examples, a second set of corrected speaker identities is predicted using the predicted audio features and the first set of corrected speaker IDs at 624. Other post-processing may be performed at 626 after the second set of speaker identities is predicted.

The transcribed audio is output at 628 according to the request. Additionally, one or more services may consume the transcription and perform one or more acts with the transcription.

As noted above, ITN, punction, and/or casing are used to convert ASR outputs into a written format. In some examples, ITN, punction, and/or casing benefit from the speaker turn information by diarization since there will likely be casing changes and punctuations around speaker turns. Moreover, all of these systems need lexical context and can make use of common pre-trained language models to refine the ASR and/or diarization outputs. In some instances, it may be beneficial to have a common system to correct speaker errors as well as to convert the spoken form to written form. Many text sequence-to-sequence (S2S) models that are based on an encoder-decoder approach are pre-trained on tasks like summarization, machine translation, textual similarity, etc. and have strong lexical knowledge. This lexical knowledge can be leveraged with tokens for speaker labels to perform ITN, speaker error correction, etc.

Figure 7:
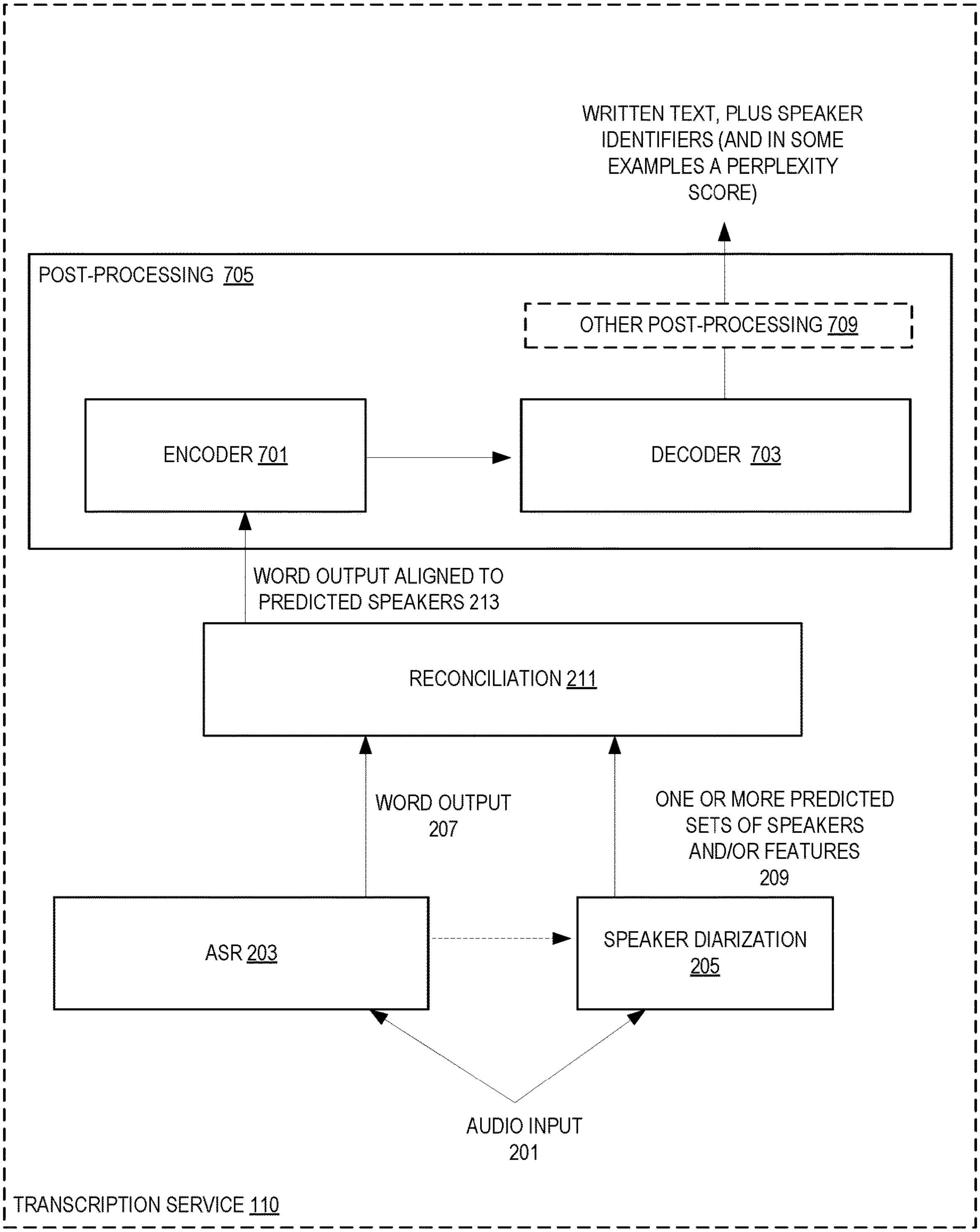
FIG. 7 illustrates examples of a transcription service that utilizes an encoder-decoder architecture to perform post-processing.

FIG. 7 illustrates examples of a transcription service that utilizes an encoder-decoder architecture to perform post-processing. This post-processing generates written text that is cased and/or punctuated and performs speaker diarization correction. In this figure, components that are not different than FIG. 2 use the same numbering. As detailed above, the reconciliation component 211 produces a word output that is aligned to predicted speakers 213. In some examples, there is a per word speaker alignment. In some examples, the speaker alignment is at a turn.

The word output that is aligned to predicted speakers 213 is subjected to post-processing 705. In particular, the word output that is aligned to predicted speakers 213 is provided to an encoder 701 which has been trained to predict contextual joint speaker and (spoken form) word embeddings (features). The joint speaker and word embeddings are provided to an autoregressive decoder 703 that attends to the embeddings along with the output words from a previous timestamp to produce the written form words along with corrected speaker labels until an end of sentence (EOS) token is reached. The output of the decoder 703 is a written form (e.g., ITNed, cased, and/or punctuated) of the input to the encoder 701 and corrected speaker labels. In some examples, the encoder-decoder architecture is Transformer-based (e.g., BART, T5, etc.).

In some examples, other post-processing 709 is performed to perform ITN, punctuation, speaker perplexity, and/or casing if that is not performed by the decoder 703.

Figure 8:
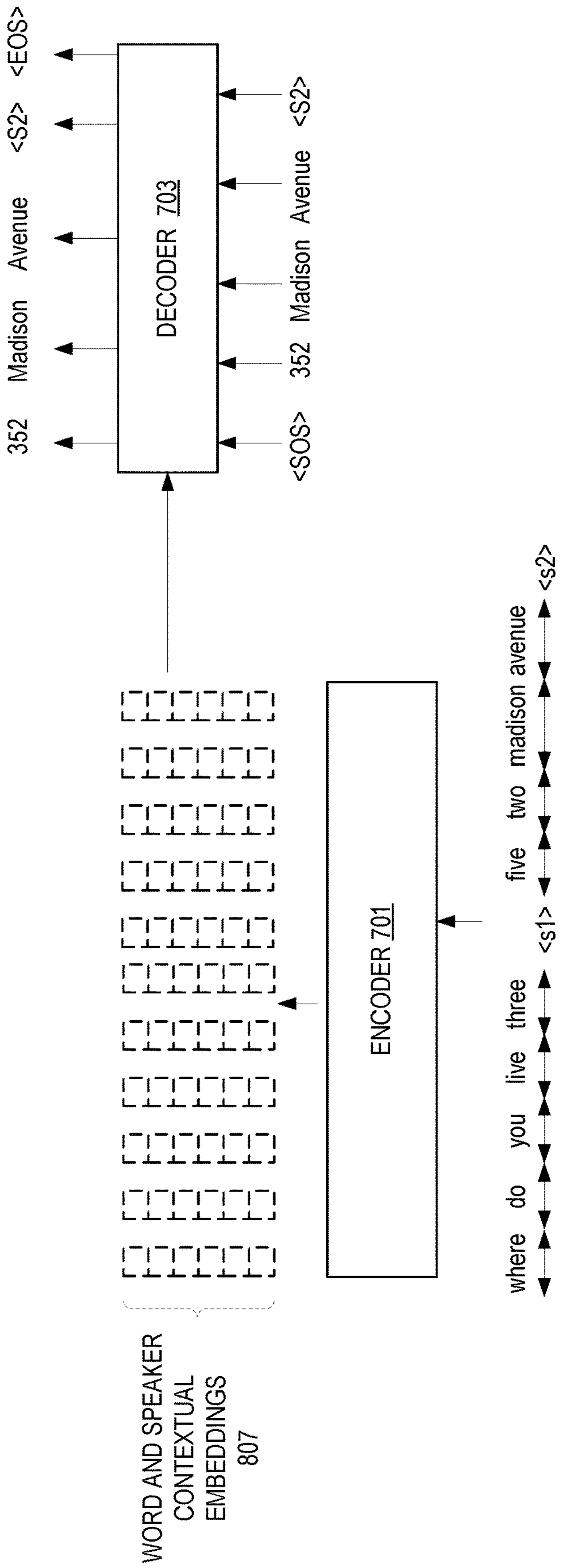
FIG. 8 illustrates examples of post-processing.

FIG. 8 illustrates examples of post-processing 705. In this example, the encoder 701 is fed a word output that is aligned to predicted speakers of "where do you live three <s1> five two madison avenue <s2>." In this example text, it would be clear to an English speaking person that "where to you live" forms a question and that is likely where there would be a speaker turn (from speaker 1 (<s1>) to speaker 2 (<s2>). Clearly, that is not what the reconciled output was, however. Note too that at this point there has been no casing, etc. to the prediction of the spoken words and speakers.

The encoder 701 predicts contextual joint speaker and (spoken form) word embeddings 807 from the input text. These embeddings 807 are provided to the autoregressive decoder 703, along with the output words from a previous timestamp, for the decoder 703 to produce the written form words along with corrected speaker labels. Note that the written form has changed the text numbers to a numeric representation. In this particular example, punctuation has not been added by the decoder 703. However, in some examples, before the <s2> output punctuation is added (such as a period). In some examples, other post-processing 709 is performed to add punction or casing.

FIG. 9 is a flow diagram illustrating operations of a method for transcribing audio according to some examples. Some or all of the operations (or other processes described herein, or variations, and/or combinations thereof) are performed under the control of one or more computer systems configured with executable instructions, and are implemented as code (e.g., executable instructions, one or more computer programs, or one or more applications) executing collectively on one or more processors. The code is stored on a computer-readable storage medium, for example, in the form of a computer program comprising instructions executable by one or more processors. The computer-readable storage medium is non-transitory. In some examples, one or more (or all) of the operations are performed by the transcription service 110 of the other figures.

In some examples, a transcription system is trained at 902. In some examples, this training includes training of one or more of an ASR, a SD, and/or a speaker error corrector. The training may include the re-training of one or more of the models for those components.

A request to transcribe audio is received at 904. The request includes one or more of: an indication of a source of the audio (e.g., a location of a file, a location of a stream, etc.), an indication of a language of the audio, an indication of a location to store the transcription, an indication of where to provide the transcription, an indication of a model to use for ASR, SD, etc., The audio is transcribed according to the request using a SEC at 906. The transcription may include one or more acts. The words in the audio are predicted using ASR at 908. For example, an ASR model is applied to the audio. Note that in some examples a particular ASR model is used if so indicated by the request.

One or more speakers in the audio are predicted at 910. For example, SD is performed. In some examples, features are also determined.

The words of the audio are reconciled with the predicted one or more speakers to generate word output that is aligned to the predicted speakers at 912.

Post-processing is then performed at 913. In some examples, when there is only one predicted speaker, other non-SEC post-processing is performed such as ITN, casing, and punctuation inclusion at 920. In some examples, when there are more predicted speakers than the SEC is trained to handle, other non-SEC post-processing is performed at 929.

In some examples, joint speaker error correction and at least ITN is performed on the word output that is aligned to the predicted speakers at 914. In some examples, word and speaker features are predicted using an encoder at 916. The features are provided to an autoregressive decoder which predicts at least ITN corrected text (written form text) along with corrected speaker identifiers at 918. The autoregressive decoder is also fed a tokenized input sequence (e.g., a token for start of sentence (SOS), followed by the output token generated from embeddings and SOS token, etc.). In some examples, the autoregressive decoder is also trained to predict one or more of punctuation and casing.

Other post-processing may be performed at 929 for items the autoregressive decoder is not trained to perform. For example, if the autoregressive decoder is not trained to predict one or more of punctuation and casing, one or more other models are used to predict one or more of punctuation and casing.

The transcribed audio is output at 928 according to the request. Additionally, one or more services may consume the transcription and perform one or more acts with the transcription.

Figure 10:
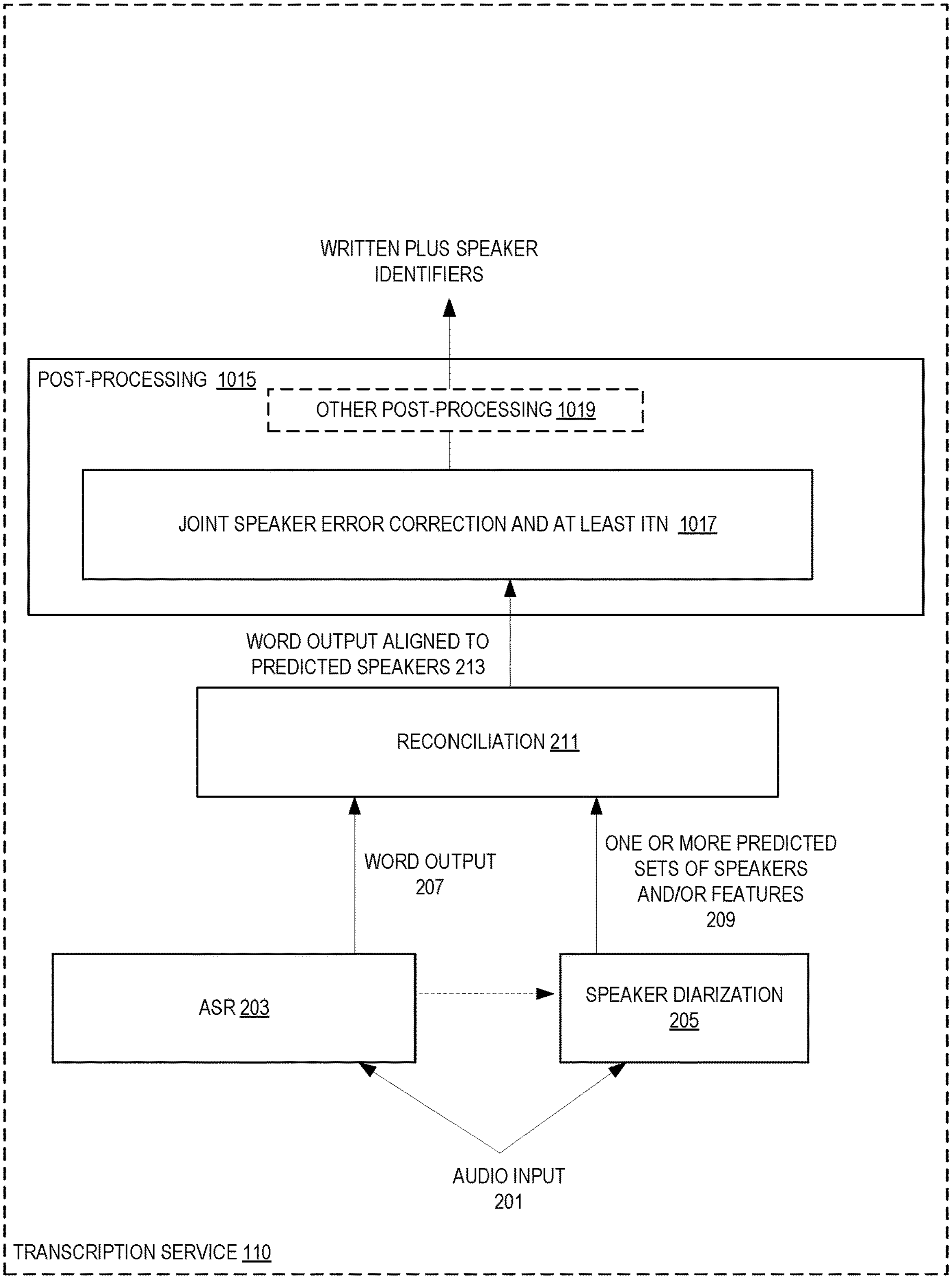
FIG. 10 illustrates examples of a transcription service that utilizes an encoder-decoder architecture to perform post-processing.

FIG. 10 illustrates examples of a transcription service that utilizes an encoder-decoder architecture to perform post-processing. This post-processing generates written text that is cased and/or punctuated and performs speaker diarization correction. In this figure, components that are not different than FIG. 2 use the same numbering. As detailed above, the reconciliation component 211 produces a word output that is aligned to predicted speakers 213. In some examples, there is a per word speaker alignment. In some examples, the speaker alignment is at a turn.

The word output that is aligned to predicted speakers 213 is subjected to post-processing 1015. In particular, the word output that is aligned to predicted speakers 213 is provided to a joint speaker error correction and at least ITN component 1017. In some examples, other post-processing such as one or more of punctuation, speaker perplexity, and/or casing is performed after the joint speaker error correction and at least ITN prediction.

Figure 11:
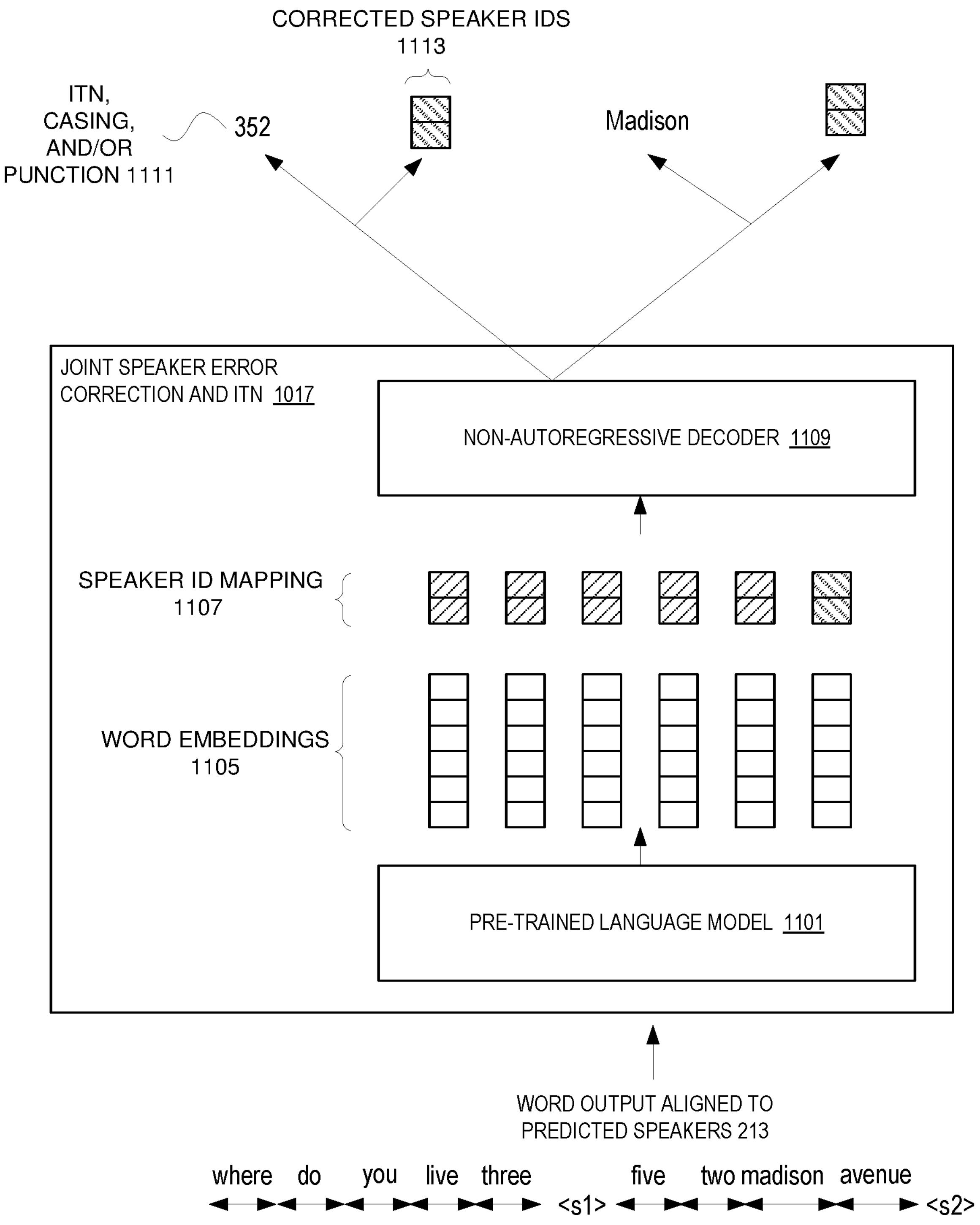
FIG. 11 illustrates examples of the joint speaker error correction and at least ITN component.

FIG. 11 illustrates examples of the joint speaker error correction and at least ITN component 1017. As illustrated, examples of the joint speaker error correction and at least ITN component 1017 include a pre-trained language model 1101 (illustrative types of pre-trained language models have been discussed above with at least respect to pre-trained language model 401) and a non-autoregressive decoder 1109.

The pre-trained language model 1101 takes in the word output $W_i$ that is aligned to detected speakers (e.g., the reconciliation output 213) to generate contextual word embeddings 405 (e.g., $$\{E_j\}_{j=1}^{M}, E_i \in \mathbb{R}^{1\times W},$$

where M is the number of tokens in the word sequence and W is the word embedding dimension). In some examples, the word output $W_i$ is tokenized prior to the LM 1101. The LM 1101 also maps word level speaker labels $S_i$ to a token level by mapping a speaker ID corresponding to the word to its first token when the word has more than two tokens and a "don't care" token is assigned to any subsequent tokens of the word. This is shown as token level speaker ID mapping 1107.

The word embeddings 1105 and token level speaker ID mapping 1107 are fed into a non-autoregressive decoder 1109 that has a plurality of heads. In some examples, the non-autoregressive decoder 1109 has two heads—one for words (to generate ITN, casing, and/or punctuation 1111) and one for speaker labels (to predict corrected speaker IDS 1113). The use of the non-autoregressive decoder 1109 may allow for faster inference using additional context of past and future words.

FIG. 12 is a flow diagram illustrating operations of a method for transcribing audio according to some examples. Some or all of the operations (or other processes described herein, or variations, and/or combinations thereof) are performed under the control of one or more computer systems configured with executable instructions, and are implemented as code (e.g., executable instructions, one or more computer programs, or one or more applications) executing collectively on one or more processors. The code is stored on a computer-readable storage medium, for example, in the form of a computer program comprising instructions executable by one or more processors. The computer-readable storage medium is non-transitory. In some examples, one or more (or all) of the operations are performed by the transcription service 110 of the other figures.

In some examples, a transcription system is trained at 1202. In some examples, this training includes training of one or more of an ASR, a SD, and/or a speaker error corrector. The training may include the re-training of one or more of the models for those components.

A request to transcribe audio is received at 1204. The request includes one or more of: an indication of a source of the audio (e.g., a location of a file, a location of a stream, etc.), an indication of a language of the audio, an indication of a location to store the transcription, an indication of where to provide the transcription, an indication of a model to use for ASR, SD, etc., The audio is transcribed according to the request using a SEC at 1206. The transcription may include one or more acts. The words in the audio are predicted using ASR at 1208. For example, an ASR model is applied to the audio. Note that in some examples a particular ASR model is used if so indicated by the request.

One or more speakers in the audio are predicted at 1210. For example, SD is performed. In some examples, features are also determined.

The words of the audio are reconciled with the predicted one or more speakers to generate word output that is aligned to the predicted speakers at 1212.

Post-processing is then performed at 1213. In some examples, when there is only one predicted speaker, other non-SEC post-processing is performed such as ITN and punctuation inclusion at 1222. In some examples, when there are more predicted speakers than the SEC is trained to handle, other non-SEC post-processing is performed at 1222.

In some examples, speaker error correction is performed on the word output that is aligned to the predicted speakers at 1214.

Lexical error correction is performed on the word output that is aligned to the predicted speakers. In some examples, the lexical error correction utilizes a pre-trained language model to generate word or sub-word embeddings at 1216 which are then mapped to speaker identifiers at 1218. The (sub-) word embeddings and mapped speaker identifiers are provided to a non-autoregressive decoder to predict at least ITN corrected text and corrected speaker identifiers at 1220.

Other post-processing may be performed at 1222 (e.g., casing and/or punctuation if that is not performed at 1220.

The transcribed audio is output at 1224 according to the request. Additionally, one or more services may consume the transcription and perform one or more acts with the transcription.

Figure 13:
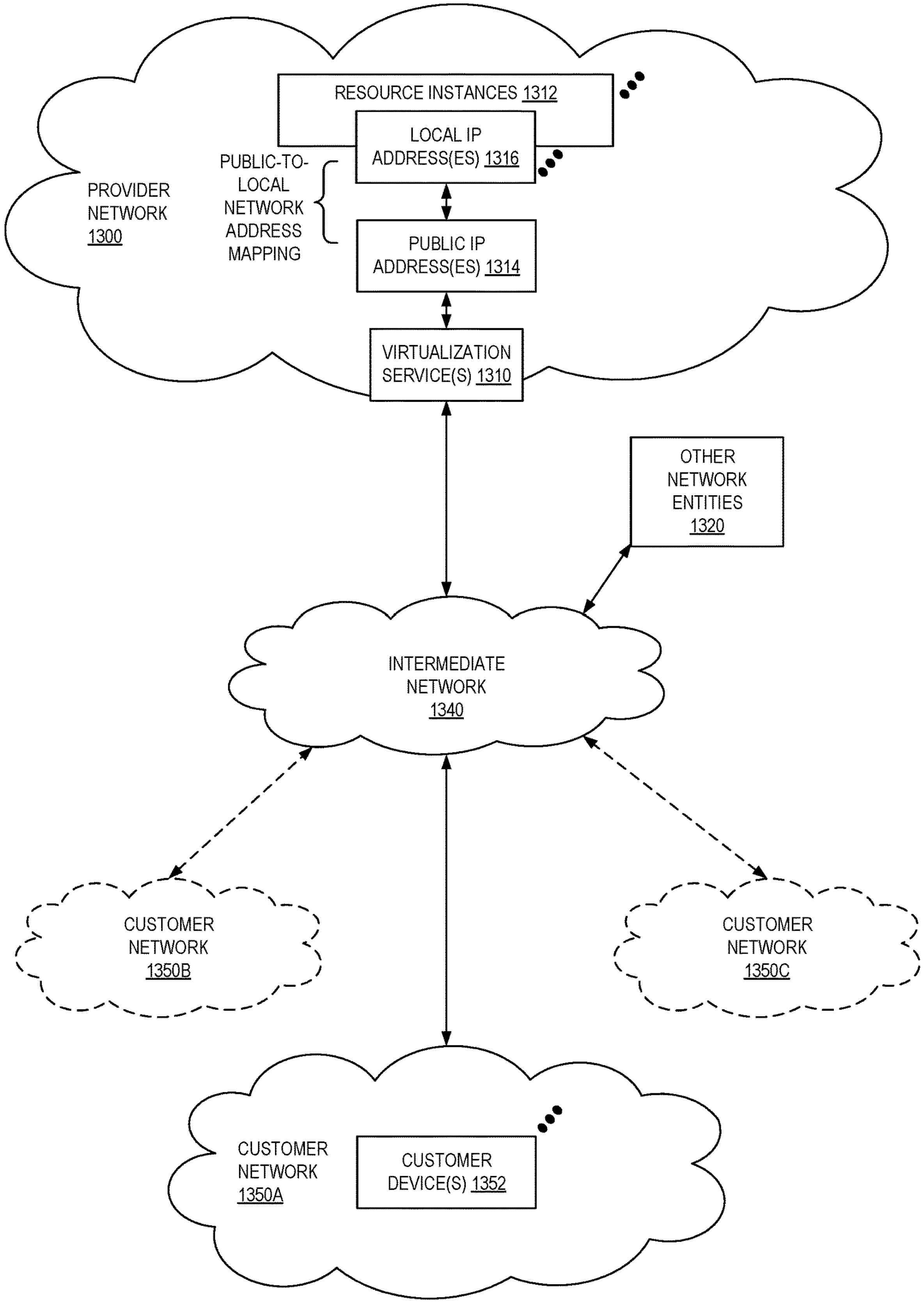
FIG. 13 illustrates an example provider network environment according to some examples.

FIG. 13 illustrates an example provider network (or "service provider system") environment according to some examples. A provider network 1300 can provide resource virtualization to customers via one or more virtualization services 1310 that allow customers to purchase, rent, or otherwise obtain instances 1312 of virtualized resources, including but not limited to computation and storage resources, implemented on devices within the provider network or networks in one or more data centers. Local Internet Protocol (IP) addresses 1316 can be associated with the resource instances 1312; the local IP addresses are the internal network addresses of the resource instances 1312 on the provider network 1300. In some examples, the provider network 1300 can also provide public IP addresses 1314 and/or public IP address ranges (e.g., Internet Protocol version 4 (IPv4) or Internet Protocol version 6 (IPv6) addresses) that customers can obtain from the provider 1300.

Conventionally, the provider network 1300, via the virtualization services 1310, can allow a customer of the service provider (e.g., a customer that operates one or more customer networks 1350A-1350C (or "client networks") including one or more customer device(s) 1352) to dynamically associate at least some public IP addresses 1314 assigned or allocated to the customer with particular resource instances 1312 assigned to the customer. The provider network 1300 can also allow the customer to remap a public IP address 1314, previously mapped to one virtualized computing resource instance 1312 allocated to the customer, to another virtualized computing resource instance 1312 that is also allocated to the customer. Using the virtualized computing resource instances 1312 and public IP addresses 1314 provided by the service provider, a customer of the service provider such as the operator of the customer network(s) 1350A-1350C can, for example, implement customer-specific applications and present the customer's applications on an intermediate network 1340, such as the Internet. Other network entities 1320 on the intermediate network 1340 can then generate traffic to a destination public IP address 1314 published by the customer network(s) 1350A-1350C; the traffic is routed to the service provider data center, and at the data center is routed, via a network substrate, to the local IP address 1316 of the virtualized computing resource instance 1312 currently mapped to the destination public IP address 1314. Similarly, response traffic from the virtualized computing resource instance 1312 can be routed via the network substrate back onto the intermediate network 1340 to the source entity 1320.

Local IP addresses, as used herein, refer to the internal or "private" network addresses, for example, of resource instances in a provider network. Local IP addresses can be within address blocks reserved by Internet Engineering Task Force (IETF) Request for Comments (RFC) 1918 and/or of an address format specified by IETF RFC 4193 and can be mutable within the provider network. Network traffic originating outside the provider network is not directly routed to local IP addresses; instead, the traffic uses public IP addresses that are mapped to the local IP addresses of the resource instances. The provider network can include networking devices or appliances that provide network address translation (NAT) or similar functionality to perform the mapping from public IP addresses to local IP addresses and vice versa.

Public IP addresses are Internet mutable network addresses that are assigned to resource instances, either by the service provider or by the customer. Traffic routed to a public IP address is translated, for example via 1:1 NAT, and forwarded to the respective local IP address of a resource instance.

Some public IP addresses can be assigned by the provider network infrastructure to particular resource instances; these public IP addresses can be referred to as standard public IP addresses, or simply standard IP addresses. In some examples, the mapping of a standard IP address to a local IP address of a resource instance is the default launch configuration for all resource instance types.

At least some public IP addresses can be allocated to or obtained by customers of the provider network 1300; a customer can then assign their allocated public IP addresses to particular resource instances allocated to the customer. These public IP addresses can be referred to as customer public IP addresses, or simply customer IP addresses. Instead of being assigned by the provider network 1300 to resource instances as in the case of standard IP addresses, customer IP addresses can be assigned to resource instances by the customers, for example via an API provided by the service provider. Unlike standard IP addresses, customer IP addresses are allocated to customer accounts and can be remapped to other resource instances by the respective customers as necessary or desired. A customer IP address is associated with a customer's account, not a particular resource instance, and the customer controls that IP address until the customer chooses to release it. Unlike conventional static IP addresses, customer IP addresses allow the customer to mask resource instance or availability zone failures by remapping the customer's public IP addresses to any resource instance associated with the customer's account. The customer IP addresses, for example, enable a customer to engineer around problems with the customer's resource instances or software by remapping customer IP addresses to replacement resource instances.

Figure 14:
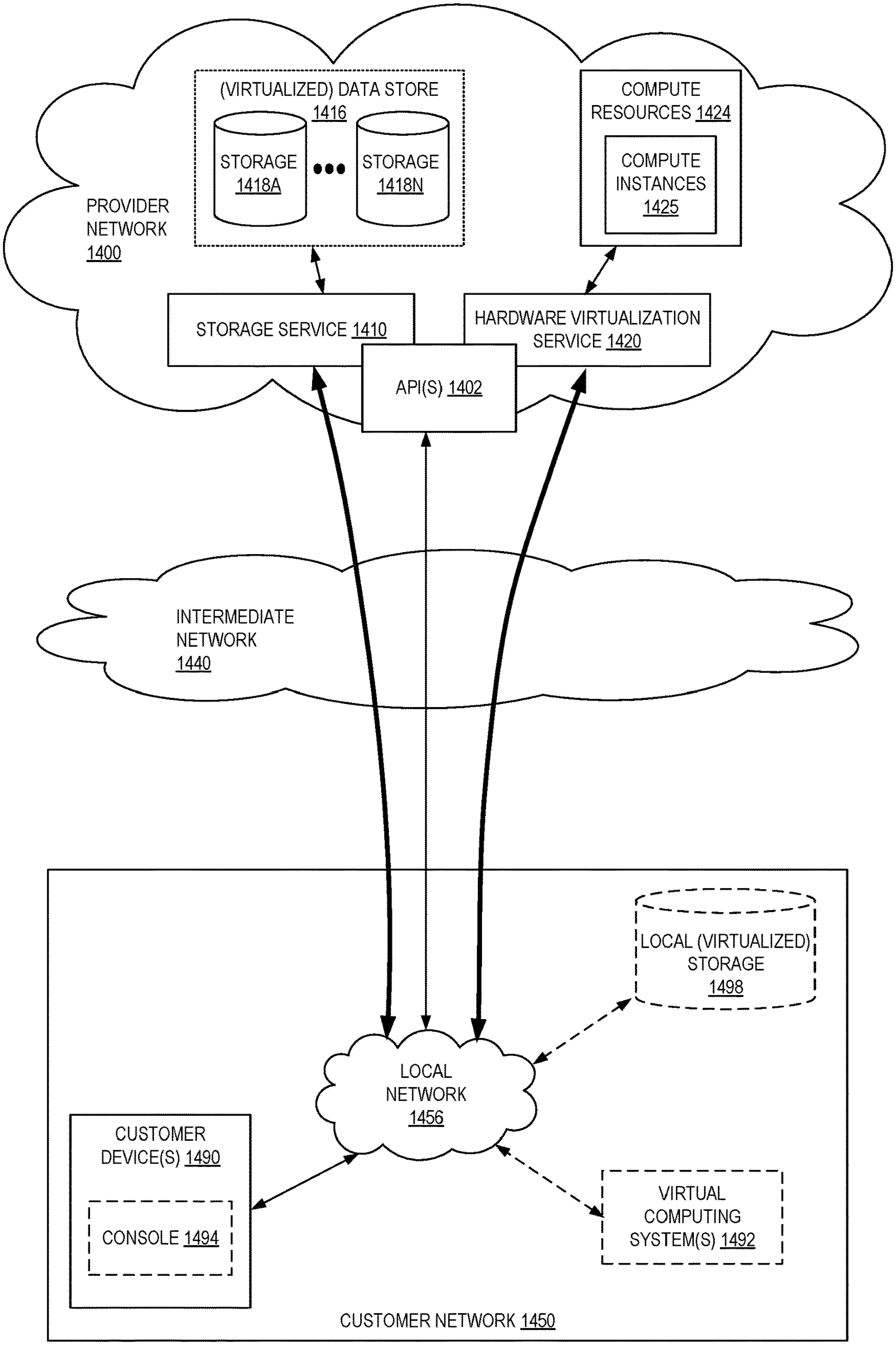
FIG. 14 is a block diagram of an example provider network that provides a storage service and a hardware virtualization service to customers according to some examples.

FIG. 14 is a block diagram of an example provider network environment that provides a storage service and a hardware virtualization service to customers, according to some examples. A hardware virtualization service 1420 provides multiple compute resources 1424 (e.g., compute instances 1425, such as VMs) to customers. The compute resources 1424 can, for example, be provided as a service to customers of a provider network 1400 (e.g., to a customer that implements a customer network 1450). Each computation resource 1424 can be provided with one or more local IP addresses. The provider network 1400 can be configured to route packets from the local IP addresses of the compute resources 1424 to public Internet destinations, and from public Internet sources to the local IP addresses of the compute resources 1424.

The provider network 1400 can provide the customer network 1450, for example coupled to an intermediate network 1440 via a local network 1456, the ability to implement virtual computing systems 1492 via the hardware virtualization service 1420 coupled to the intermediate network 1440 and to the provider network 1400. In some examples, the hardware virtualization service 1420 can provide one or more APIs 1402, for example a web services interface, via which the customer network 1450 can access functionality provided by the hardware virtualization service 1420, for example via a console 1494 (e.g., a web-based application, standalone application, mobile application, etc.) of a customer device 1490. In some examples, at the provider network 1400, each virtual computing system 1492 at the customer network 1450 can correspond to a computation resource 1424 that is leased, rented, or otherwise provided to the customer network 1450.

From an instance of the virtual computing system(s) 1492 and/or another customer device 1490 (e.g., via console 1494), the customer can access the functionality of a storage service 1410, for example via the one or more APIs 1402, to access data from and store data to storage resources 1418A-1418N of a virtual data store 1416 (e.g., a folder or "bucket," a virtualized volume, a database, etc.) provided by the provider network 1400. In some examples, a virtualized data store gateway (not shown) can be provided at the customer network 1450 that can locally cache at least some data, for example frequently accessed or critical data, and that can communicate with the storage service 1410 via one or more communications channels to upload new or modified data from a local cache so that the primary store of data (the virtualized data store 1416) is maintained. In some examples, a user, via the virtual computing system 1492 and/or another customer device 1490, can mount and access virtual data store 1416 volumes via the storage service 1410 acting as a storage virtualization service, and these volumes can appear to the user as local (virtualized) storage 1498.

While not shown in FIG. 14, the virtualization service(s) can also be accessed from resource instances within the provider network 1400 via the API(s) 1402. For example, a customer, appliance service provider, or other entity can access a virtualization service from within a respective virtual network on the provider network 1400 via the API(s) 1402 to request allocation of one or more resource instances within the virtual network or within another virtual network.

Illustrative Systems

Figure 15:
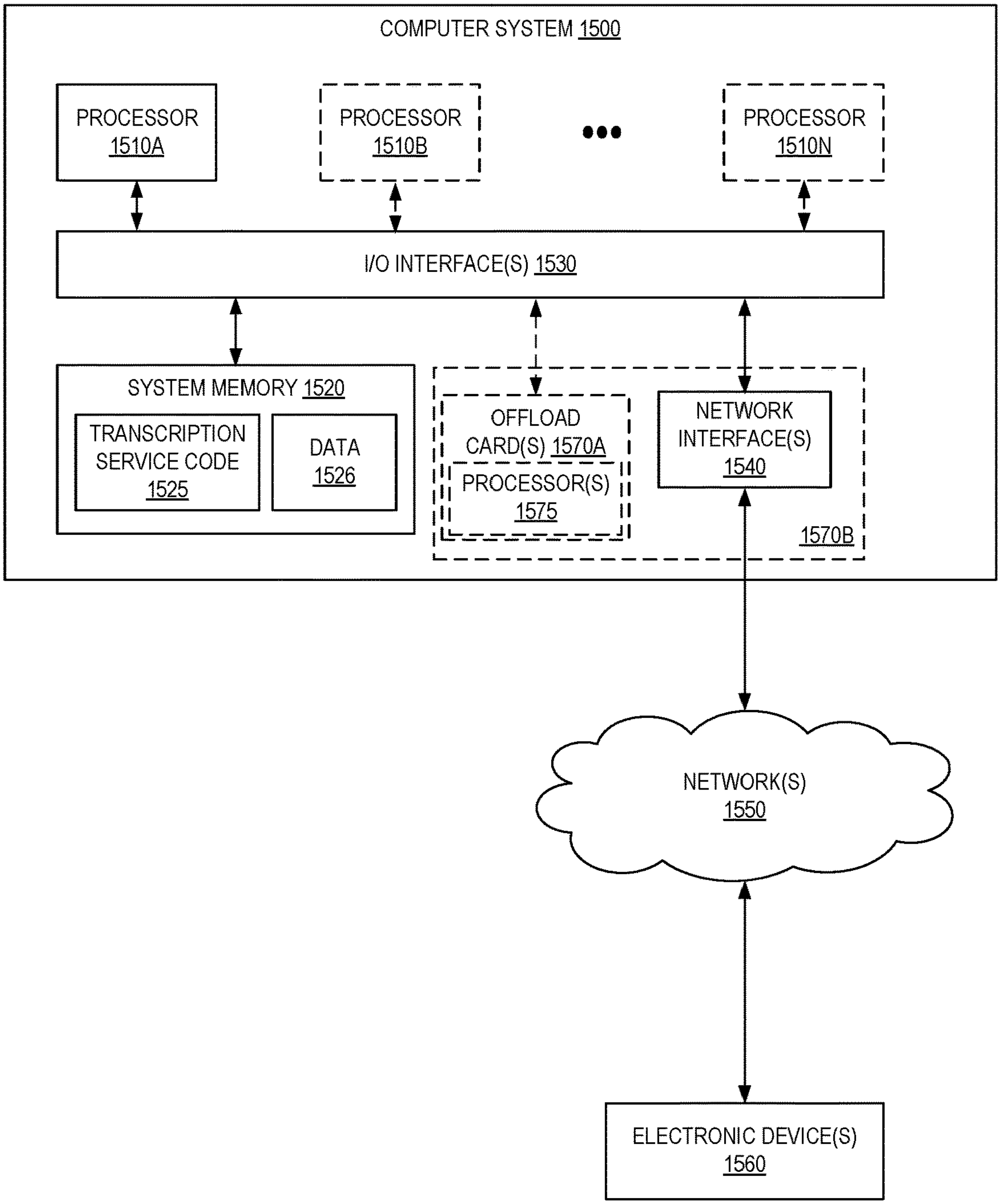
FIG. 15 is a block diagram illustrating an example computer system that can be used in some examples.

In some examples, a system that implements a portion or all of the techniques described herein can include a general-purpose computer system, such as the computer system 1500 (also referred to as a computing device or electronic device) illustrated in FIG. 15, that includes, or is configured to access, one or more computer-accessible media. In the illustrated example, the computer system 1500 includes one or more processors 1510 coupled to a system memory 1520 via an input/output (I/O) interface 1530. The computer system 1500 further includes a network interface 1540 coupled to the I/O interface 1530. While FIG. 15 shows the computer system 1500 as a single computing device, in various examples the computer system 1500 can include one computing device or any number of computing devices configured to work together as a single computer system 1500.

In various examples, the computer system 1500 can be a uniprocessor system including one processor 1510, or a multiprocessor system including several processors 1510 (e.g., two, four, eight, or another suitable number). The processor(s) 1510 can be any suitable processor(s) capable of executing instructions. For example, in various examples, the processor(s) 1510 can be general-purpose or embedded processors implementing any of a variety of instruction set architectures (ISAs), such as the x86, ARM, PowerPC, SPARC, or MIPS ISAs, or any other suitable ISA. In multiprocessor systems, each of the processors 1510 can commonly, but not necessarily, implement the same ISA.

The system memory 1520 can store instructions and data accessible by the processor(s) 1510. In various examples, the system memory 1520 can be implemented using any suitable memory technology, such as random-access memory (RAM), static RAM (SRAM), synchronous dynamic RAM (SDRAM), nonvolatile/Flash-type memory, or any other type of memory. In the illustrated example, program instructions and data implementing one or more desired functions, such as those methods, techniques, and data described above, are shown stored within the system memory 1520 as transcription service code 1525 (e.g., executable to implement, in whole or in part, the transcription service 110) and data 1526.

In some examples, the I/O interface 1530 can be configured to coordinate I/O traffic between the processor 1510, the system memory 1520, and any peripheral devices in the device, including the network interface 1540 and/or other peripheral interfaces (not shown). In some examples, the I/O interface 1530 can perform any necessary protocol, timing, or other data transformations to convert data signals from one component (e.g., the system memory 1520) into a format suitable for use by another component (e.g., the processor 1510). In some examples, the I/O interface 1530 can include support for devices attached through various types of peripheral buses, such as a variant of the Peripheral Component Interconnect (PCI) bus standard or the Universal Serial Bus (USB) standard, for example. In some examples, the function of the I/O interface 1530 can be split into two or more separate components, such as a north bridge and a south bridge, for example. Also, in some examples, some or all of the functionality of the I/O interface 1530, such as an interface to the system memory 1520, can be incorporated directly into the processor 1510.

The network interface 1540 can be configured to allow data to be exchanged between the computer system 1500 and other devices 1560 attached to a network or networks 1550, such as other computer systems or devices as illustrated in FIG. 1, for example. In various examples, the network interface 1540 can support communication via any suitable wired or wireless general data networks, such as types of Ethernet network, for example. Additionally, the network interface 1540 can support communication via telecommunications/telephony networks, such as analog voice networks or digital fiber communications networks, via storage area networks (SANs), such as Fibre Channel SANs, and/or via any other suitable type of network and/or protocol.

In some examples, the computer system 1500 includes one or more offload cards 1570A or 1570B (including one or more processors 1575, and possibly including the one or more network interfaces 1540) that are connected using the I/O interface 1530 (e.g., a bus implementing a version of the Peripheral Component Interconnect Express (PCI-E) standard, or another interconnect such as a QuickPath interconnect (QPI) or UltraPath interconnect (UPI)). For example, in some examples the computer system 1500 can act as a host electronic device (e.g., operating as part of a hardware virtualization service) that hosts compute resources such as compute instances, and the one or more offload cards 1570A or 1570B execute a virtualization manager that can manage compute instances that execute on the host electronic device. As an example, in some examples the offload card(s) 1570A or 1570B can perform compute instance management operations, such as pausing and/or un-pausing compute instances, launching and/or terminating compute instances, performing memory transfer/copying operations, etc. These management operations can, in some examples, be performed by the offload card(s) 1570A or 1570B in coordination with a hypervisor (e.g., upon a request from a hypervisor) that is executed by the other processors 1510A-1510N of the computer system 1500. However, in some examples the virtualization manager implemented by the offload card(s) 1570A or 1570B can accommodate requests from other entities (e.g., from compute instances themselves), and cannot coordinate with (or service) any separate hypervisor.

In some examples, the system memory 1520 can be one example of a computer-accessible medium configured to store program instructions and data as described above. However, in other examples, program instructions and/or data can be received, sent, or stored upon different types of computer-accessible media. Generally speaking, a computer-accessible medium can include any non-transitory storage media or memory media such as magnetic or optical media, e.g., disk or DVD/CD coupled to the computer system 1500 via the I/O interface 1530. A non-transitory computer-accessible storage medium can also include any volatile or non-volatile media such as RAM (e.g., SDRAM, double data rate (DDR) SDRAM, SRAM, etc.), read only memory (ROM), etc., that can be included in some examples of the computer system 1500 as the system memory 1520 or another type of memory. Further, a computer-accessible medium can include transmission media or signals such as electrical, electromagnetic, or digital signals, conveyed via a communication medium such as a network and/or a wireless link, such as can be implemented via the network interface 1540.

Various examples discussed or suggested herein can be implemented in a wide variety of operating environments, which in some cases can include one or more user computers, computing devices, or processing devices which can be used to operate any of a number of applications. User or client devices can include any of a number of general-purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially available operating systems and other known applications for purposes such as development and database management. These devices also can include other electronic devices, such as dummy terminals, thin-clients, gaming systems, and/or other devices capable of communicating via a network.

Most examples use at least one network that would be familiar to those skilled in the art for supporting communications using any of a variety of widely-available protocols, such as Transmission Control Protocol/Internet Protocol (TCP/IP), File Transfer Protocol (FTP), Universal Plug and Play (UPnP), Network File System (NFS), Common Internet File System (CIFS), Extensible Messaging and Presence Protocol (XMPP), AppleTalk, etc. The network(s) can include, for example, a local area network (LAN), a wide-area network (WAN), a virtual private network (VPN), the Internet, an intranet, an extranet, a public switched telephone network (PSTN), an infrared network, a wireless network, and any combination thereof.

In examples using a web server, the web server can run any of a variety of server or mid-tier applications, including HTTP servers, File Transfer Protocol (FTP) servers, Common Gateway Interface (CGI) servers, data servers, Java servers, business application servers, etc. The server(s) also can be capable of executing programs or scripts in response requests from user devices, such as by executing one or more Web applications that can be implemented as one or more scripts or programs written in any programming language, such as Java®, C, C# or C++, or any scripting language, such as Perl, Python, PHP, or TCL, as well as combinations thereof. The server(s) can also include database servers, including without limitation those commercially available from Oracle®, Microsoft®, Sybase®, IBM®, etc. The database servers can be relational or non-relational (e.g., "NoSQL"), distributed or non-distributed, etc.

Environments disclosed herein can include a variety of data stores and other memory and storage media as discussed above. These can reside in a variety of locations, such as on a storage medium local to (and/or resident in) one or more of the computers or remote from any or all of the computers across the network. In a particular set of examples, the information can reside in a storage-area network (SAN) familiar to those skilled in the art. Similarly, any necessary files for performing the functions attributed to the computers, servers, or other network devices can be stored locally and/or remotely, as appropriate. Where a system includes computerized devices, each such device can include hardware elements that can be electrically coupled via a bus, the elements including, for example, at least one central processing unit (CPU), at least one input device (e.g., a mouse, keyboard, controller, touch screen, or keypad), and/or at least one output device (e.g., a display device, printer, or speaker). Such a system can also include one or more storage devices, such as disk drives, optical storage devices, and solid-state storage devices such as random-access memory (RAM) or read-only memory (ROM), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or web browser. It should be appreciated that alternate examples can have numerous variations from that described above. For example, customized hardware might also be used and/or particular elements might be implemented in hardware, software (including portable software, such as applets), or both. Further, connection to other computing devices such as network input/output devices can be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory (EEPROM), flash memory or other memory technology, Compact Disc-Read Only Memory (CD-ROM), Digital Versatile Disk (DVD) or other optical storage, magnetic cassettes, magnetic tape, magnetic disk storage or other magnetic storage devices, or any other medium which can be used to store the desired information and which can be accessed by a system device. Based on the disclosure and teachings provided herein, a person of ordinary skill in the art will appreciate other ways and/or methods to implement the various examples.

In the preceding description, various examples are described. For purposes of explanation, specific configurations and details are set forth in order to provide a thorough understanding of the examples. However, it will also be apparent to one skilled in the art that the examples can be practiced without the specific details. Furthermore, well-known features can be omitted or simplified in order not to obscure the example being described.

Bracketed text and blocks with dashed borders (e.g., large dashes, small dashes, dot-dash, and dots) are used herein to illustrate optional aspects that add additional features to some examples. However, such notation should not be taken to mean that these are the only options or optional operations, and/or that blocks with solid borders are not optional in certain examples.

Reference numerals with suffix letters (e.g., 1418A-1418N) can be used to indicate that there can be one or multiple instances of the referenced entity in various examples, and when there are multiple instances, each does not need to be identical but may instead share some general traits or act in common ways. Further, the particular suffixes used are not meant to imply that a particular amount of the entity exists unless specifically indicated to the contrary. Thus, two entities using the same or different suffix letters might or might not have the same number of instances in various examples.

References to "one example," "an example," etc., indicate that the example described may include a particular feature, structure, or characteristic, but every example may not necessarily include the particular feature, structure, or characteristic. Moreover, such phrases are not necessarily referring to the same example. Further, when a particular feature, structure, or characteristic is described in connection with an example, it is submitted that it is within the knowledge of one skilled in the art to affect such feature, structure, or characteristic in connection with other examples whether or not explicitly described.

Moreover, in the various examples described above, unless specifically noted otherwise, disjunctive language such as the phrase "at least one of A, B, or C" is intended to be understood to mean either A, B, or C, or any combination thereof (e.g., A, B, and/or C). Similarly, language such as "at least one or more of A, B, and C" (or "one or more of A, B, and C") is intended to be understood to mean A. B. or C, or any combination thereof (e.g., A, B, and/or C). As such, disjunctive language is not intended to, nor should it be understood to, imply that a given example requires at least one of A, at least one of B, and at least one of C to each be present.

As used herein, the term "based on" (or similar) is an open-ended term used to describe one or more factors that affect a determination or other action. It is to be understood that this term does not foreclose additional factors that may affect a determination or action. For example, a determination may be solely based on the factor(s) listed or based on the factor(s) and one or more additional factors. Thus, if an action A is "based on" B, it is to be understood that B is one factor that affects action A, but this does not foreclose the action from also being based on one or multiple other factors, such as factor C. However, in some instances, action A may be based entirely on B.

Unless otherwise explicitly stated, articles such as "a" or "an" should generally be interpreted to include one or multiple described items. Accordingly, phrases such as "a device configured to" or "a computing device" are intended to include one or multiple recited devices. Such one or more recited devices can be collectively configured to carry out the stated operations. For example, "a processor configured to carry out operations A, B, and C" can include a first processor configured to carry out operation A working in conjunction with a second processor configured to carry out operations B and C.

Further, the words "may" or "can" are used in a permissive sense (i.e., meaning having the potential to), rather than the mandatory sense (i.e., meaning must). The words "include," "including," and "includes" are used to indicate open-ended relationships and therefore mean including, but not limited to. Similarly, the words "have," "having." and "has" also indicate open-ended relationships, and thus mean having, but not limited to. The terms "first," "second." "third," and so forth as used herein are used as labels for the nouns that they precede, and do not imply any type of ordering (e.g., spatial, temporal, logical, etc.) unless such an ordering is otherwise explicitly indicated. Similarly, the values of such numeric labels are generally not used to indicate a required amount of a particular noun in the claims recited herein, and thus a "fifth" element generally does not imply the existence of four other elements unless those elements are explicitly included in the claim or it is otherwise made abundantly clear that they exist.

The specification and drawings are, accordingly, to be regarded in an illustrative rather than a restrictive sense. It will, however, be evident that various modifications and changes can be made thereunto without departing from the broader scope of the disclosure as set forth in the claims.

What is claimed is:

1. A computer-implemented method comprising:

transcribing, by a transcription service of a provider network, the transcription service implemented as transcription service code stored on one or more computer-readable storage media and executed by one or more processors of the provider network, audio according to a request by at least:

predicting words in the audio using an automatic speech recognition (ASR) model, predicting one or more speaker identities in the audio, reconciling the predicted one or more speakers with the predicted words to align the predicted words and predicted one or more speaker identities, and performing post-processing on the aligned predicted words and predicted one or more speaker identities, wherein the post-processing at least includes:

performing, by a lexical corrector of the executing transcription service code, lexical-based predicted speaker error correction on the aligned predicted words and the predicted one or more speaker identities to generate a first corrected set of speaker identities;

predicting, by an audio featurization sub-segmenter of the executing transcription service code, audio features of the audio; and generating, by a speaker identity corrector of the executing transcription service code, a second corrected set of speaker identities using the predicted audio features and the first corrected set of speaker identities; and outputting transcribed audio based on the post-processing, the transcribed audio including the predicted words and the second corrected set of speaker identities.

2. The computer-implemented method of claim 1, wherein the request includes one or more of: an indication of a source of the audio, a type of audio input, an indication of a language of the audio, an indication of a location to store a transcription, an indication of where to provide the transcription, or an indication of a model.

3. The computer-implemented method of claim 2, wherein the ASR model is trained for the indicated language.

4. A computer-implemented method comprising:

transcribing, by a transcription service implemented as transcription service code stored on one or more computer-readable storage media and executed by one or more processors, audio according to a request by at least:

predicting words in the audio using an automatic speech recognition (ASR) model, predicting one or more speaker identities in the audio, reconciling the predicted one or more speaker identities with the predicted words to align the predicted words and predicted one or more speaker identities, and performing post-processing on the aligned predicted words and predicted one or more speaker identities, wherein the post-processing at least includes:

performing, by a lexical corrector of the executing transcription service code, lexical-based predicted speaker error correction on the aligned predicted words and the predicted one or more speaker identities to generate a first corrected set of speaker identities, predicting, by an audio featurization sub-segmenter of the executing transcription service code, audio features of the audio, and generating, by a speaker identity corrector of the executing transcription service code, a second corrected set of speaker identities using the predicted audio features and the first corrected set of speaker identities; and outputting transcribed audio based on the post-processing, the transcribed audio including the predicted words and the second corrected set of speaker identities.

5. The computer-implemented method of claim 4, wherein the performing predicted speaker error correction on the aligned predicted words and the predicted one or more speaker identities comprises:

generating word embeddings using a pre-trained language model;

mapping the predicted one or more speaker identifiers to the word embeddings; and predicting the first corrected set of speaker identities from the mapped predicted one or more speaker identities and the word embeddings using an encoder.

6. The computer-implemented method of claim 5, wherein at least one of the pre-trained language model or the encoder is Transformer-based.

7. The computer-implemented method of claim 4, wherein the performing predicted speaker error correction on the aligned predicted words and the predicted one or more speaker identities to generate a first corrected set of speaker identities is performed when there are less than or equal to a number of speakers than a threshold, wherein the threshold is a number of speakers that the speaker error correction has been trained to handle.

8. The computer-implemented method of claim 4, wherein the post-processing is performed on sliding windows.

9. The computer-implemented method of claim 4, wherein the performing predicted speaker error correction on the aligned predicted words and the predicted one or more speaker identities to generate a first corrected set of speaker identities is performed by a selected speaker error corrector trained to handle a number of speaker identities equal to a number of predicted one or more speaker identities.

10. The computer-implemented method of claim 4, wherein the request includes one or more of: an indication of a source of the audio, a type of audio input, an indication of a language of the audio, an indication of a location to store a transcription, an indication of where to provide the transcription, or an indication of a model.

11. The computer-implemented method of claim 4, wherein the post-processing further comprises performing at least one of punctuation, casing, speaker perplexity calculation, or inverse text normalization on the predicted words.

12. The computer-implemented method of claim 4, wherein the transcribed audio is a medical transcription.

13. The computer-implemented method of claim 4, wherein the transcribed audio is used for live captioning.

14. A system comprising:

one or more electronic devices to implement a transcription service as transcription service code stored on one or more computer-readable storage media and executed by one or more processors in a multi-tenant provider network, the transcription service code including instructions that upon execution by the one or more processors cause the transcription service to:

transcribe audio according to a request by at least:

predicting words in the audio using an automatic speech recognition (ASR) model, predicting one or more speaker identities in the audio, reconciling the predicted one or more speaker identities with the predicted words to align the predicted words and predicted one or more speaker identities, and performing post-processing on the aligned predicted words and predicted one or more speaker identities, wherein the post-processing at least includes:

performing, by a lexical corrector of the executing transcription service code, lexical-based predicted speaker error correction on the aligned predicted words and the predicted one or more speaker identities to generate a first corrected set of speaker identities;

predict, by an audio featurization sub-segmenter of the executing transcription service code, audio features of the audio; and generate, by a speaker identity corrector of the executing transcription service code, a second corrected set of speaker identities using the predicted audio features and the first corrected set of speaker identities; and output transcribed audio based on the post-processing, the transcribed audio including the predicted words and the second corrected set of speaker identities.

15. The system of claim 14, wherein the request includes one or more of: an indication of a source of the audio, a type of audio input, an indication of a language of the audio, an indication of a location to store a transcription, an indication of where to provide the transcription, or an indication of a model.

16. The system of claim 14, wherein the post-processing further comprises performing at least one of punctuation, casing, speaker perplexity calculation, or inverse text normalization on the predicted words.

17. The system of claim 14, wherein the transcribed audio is used for live captioning.

18. The system of claim 14, wherein the transcribed audio is a medical transcription.

19. The system of claim 14, wherein at least one of the pre-trained language model or the encoder is Transformer-based.

20. The system of claim 14, wherein the post-processing is performed on sliding windows.

* * * * *